(12) United States Patent
Marshall et al.

(10) Patent No.: US 8,372,423 B2
(45) Date of Patent: Feb. 12, 2013

(54) IMPLANTABLE MEDICAL DEVICES HAVING MICROPOROUS SURFACE LAYERS AND METHOD FOR REDUCING FOREIGN BODY RESPONSE TO THE SAME

(75) Inventors: Andrew J Marshall, Seattle, WA (US); Michel Alvarez, Seattle, WA (US); Max Maginness, Seattle, WA (US)

(73) Assignee: Healionics Corporation, Seattle, WA (US)

( * ) Notice: Subject to any disclaimer, the term of this patent is extended or adjusted under 35 U.S.C. 154(b) by 0 days.

(21) Appl. No.: 13/082,760

(22) Filed: Apr. 8, 2011

(65) Prior Publication Data

US 2011/0257623 A1 Oct. 20, 2011

Related U.S. Application Data

(63) Continuation-in-part of application No. PCT/US2010/058078, filed on Nov. 24, 2010.

(60) Provisional application No. 61/322,282, filed on Apr. 8, 2010, provisional application No. 61/264,585, filed on Nov. 25, 2009.

(51) Int. Cl.
*A61F 13/00* (2006.01)
*A61K 9/00* (2006.01)
(52) U.S. Cl. ..................... 424/423; 424/400
(58) Field of Classification Search ............ 424/422, 424/423, 400
See application file for complete search history.

(56) References Cited

U.S. PATENT DOCUMENTS

| | | | |
|---|---|---|---|
| 2,842,775 A | 7/1958 | Pangman | 3/36 |
| 3,293,663 A | 12/1966 | Cronin | 3/36 |
| 3,852,832 A | 12/1974 | McGhan et al. | 3/36 |
| 3,929,971 A | 12/1975 | Roy | 423/308 |
| 3,938,528 A | 2/1976 | Bucalo | 128/334 C |
| 4,073,713 A | 2/1978 | Newman | 204/195 B |
| 4,223,070 A | 9/1980 | Hahn et al. | 428/407 |
| 4,264,990 A | 5/1981 | Hamas | 3/36 |
| 4,388,166 A | 6/1983 | Suzuki et al. | 204/403 |
| 4,400,833 A | 8/1983 | Kurland | 3/1 |
| 4,484,987 A | 11/1984 | Gough | 204/1 T |
| 4,673,409 A | 6/1987 | Van Kampen | 623/23 |
| 4,757,022 A | 7/1988 | Shults et al. | 435/291 |
| 4,820,303 A | 4/1989 | Brauman | 623/8 |
| 4,832,997 A | 5/1989 | Balanzat et al. | 428/131 |
| 4,902,294 A | 2/1990 | Gosserez | 623/8 |
| 4,960,425 A | 10/1990 | Yan et al. | 623/8 |
| 5,002,572 A | 3/1991 | Picha | 623/11 |
| 5,007,929 A | 4/1991 | Quaid | 623/8 |
| 5,022,942 A | 6/1991 | Yan et al. | 156/219 |
| 5,055,307 A | 10/1991 | Tsuru et al. | 424/493 |

(Continued)

FOREIGN PATENT DOCUMENTS

WO 2005/032418 4/2005
WO WO 2005032418 A2 * 4/2005

(Continued)

OTHER PUBLICATIONS

Barnsley et al., "Textured Surface Breast Implants in the Prevention of Capsular Contracture among Breast Augmentation Patients: A Meta-Analysis of Randomized Controlled Trials," *Plast. Reconstr. Surg.* 117: 2182-2190, Jun. 2006.

(Continued)

*Primary Examiner* — Abigail Fisher
(74) *Attorney, Agent, or Firm* — Seed IP Law Group PLLC

(57) ABSTRACT

This disclosure provides implantable devices coated with microporous surface layers with macrotopographic features that improve bio-integration at the interface of the implantable devices and the surrounding tissue.

28 Claims, 16 Drawing Sheets

U.S. PATENT DOCUMENTS

| | | | |
|---|---|---|---|
| 5,518,680 A | 5/1996 | Cima et al. | 264/401 |
| 5,589,176 A | 12/1996 | Seare, Jr. | 424/400 |
| 5,605,693 A | 2/1997 | Seare, Jr. | 424/400 |
| 5,624,674 A | 4/1997 | Seare, Jr. | 424/400 |
| 5,681,572 A | 10/1997 | Seare, Jr. | 424/400 |
| 5,753,014 A | 5/1998 | Van Rijn | 96/12 |
| 5,964,803 A | 10/1999 | Iversen et al. | 623/8 |
| 6,520,997 B1 | 2/2003 | Pekkarinen et al. | 623/23.72 |
| 6,702,857 B2 | 3/2004 | Brauker et al. | 623/23.76 |
| 6,857,932 B2 | 2/2005 | Chen | 450/38 |
| 6,875,386 B1 | 4/2005 | Ward et al. | 264/154 |
| 7,361,158 B1 | 4/2008 | Mooney, Jr. | 604/174 |
| 7,364,592 B2 | 4/2008 | Carr-Brendel et al. | 623/23.76 |
| 7,972,628 B2 * | 7/2011 | Ratner et al. | 424/499 |
| 2003/0074081 A1 | 4/2003 | Ayers | 623/23.5 |
| 2004/0086548 A1 | 5/2004 | St. John et al. | 424/445 |
| 2005/0031689 A1 | 2/2005 | Shults et al. | 424/473 |
| 2005/0228477 A1* | 10/2005 | Grainger et al. | 623/1.11 |
| 2006/0276831 A1 | 12/2006 | Porter et al. | 606/200 |
| 2008/0075752 A1 | 3/2008 | Ratner et al. | 424/426 |
| 2009/0048537 A1* | 2/2009 | Lydon et al. | 600/585 |
| 2011/0287078 A1* | 11/2011 | Ratner et al. | 424/422 |

FOREIGN PATENT DOCUMENTS

| | | |
|---|---|---|
| WO | WO 2011/065987 A1 | 6/2011 |

OTHER PUBLICATIONS

Brauker et al., "Neovascularization of synthetic membranes directed by membrane microarchitecture," *J Biomed Mater Res* 29: 1517-1524, 1995.

Madden et al., "Proangiogenic scaffolds as functional templates for cardiac tissue engineering," *Proc. Nat. Acad. Sci.* 107(34): 15211 (6 pages), 2010.

Marshall et al., "Biomaterials with Tightly Controlled Pore Size that Promote Vascular In-Growth," *Polymer Preprints* 45(2): 100-101, 2004.

Paul et al., "Topographical control of human macrophages by a regularly microstructured polyvinylidene fluoride surface," *Biomaterials* 29: 4056-4064, 2008.

Rosengren et al., "Pore size in implanted polypropylene filters is critical for tissue organization," *J Biomed Mater Res* 67A: 918-926, 2003.

Sharkawy et al., "Engineering the tissue which encapsulates subcutaneous implants. II. Plasma-tissue exchange properties," *J Biomed Mater Res* 40: 586-597, 1998.

Tsai, "Engineering biomaterial interfaces to control foreign body response: reducing giant cell formation and understanding host response to porous materials," Ph.D. Dissertation, University of Washington, 2007 (151 pages).

* cited by examiner

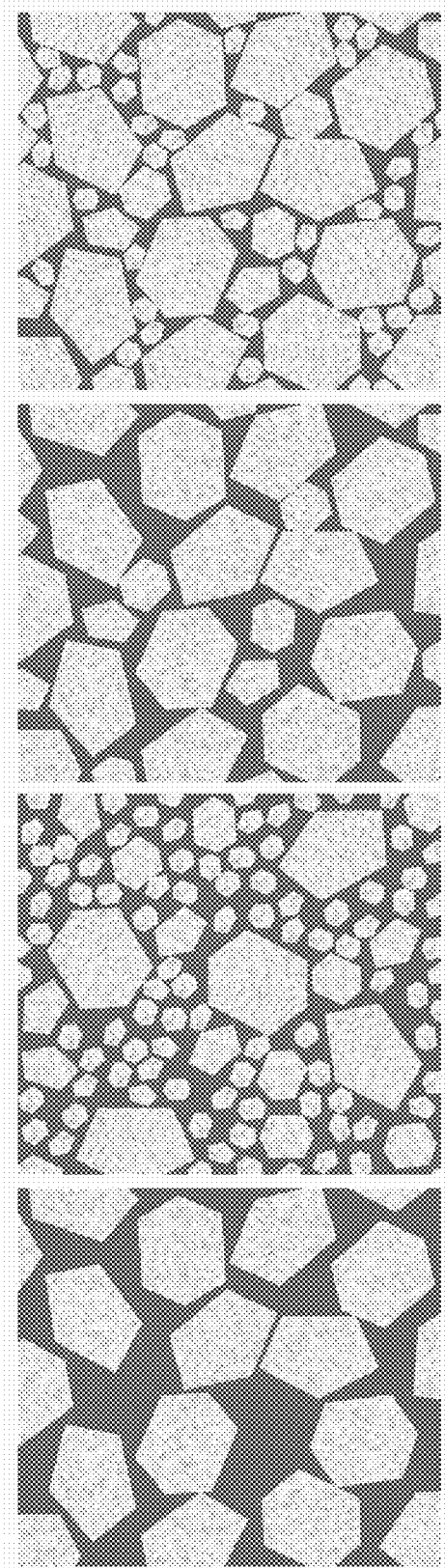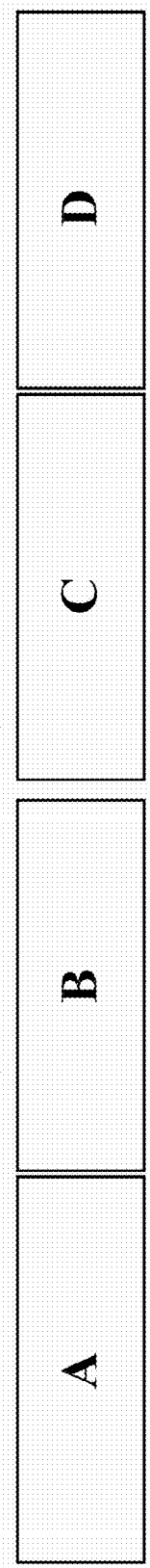
*FIG. 7*

IMPLANTABLE MEDICAL DEVICES HAVING MICROPOROUS SURFACE LAYERS AND METHOD FOR REDUCING FOREIGN BODY RESPONSE TO THE SAME

CROSS-REFERENCES TO RELATED APPLICATIONS

This application claims the benefit under 35 U.S.C. §119 (e) of U.S. Provisional Patent Application No. 61/322,282, filed Apr. 8, 2010; this application is also a continuation-in-part of International Application No. PCT/US2010/058078, filed Nov. 24, 2010, now pending. Both of the above applications are incorporated herein by reference in their entireties.

BACKGROUND

1. Technical Field

This disclosure relates to surface-coated implantable medical devices.

2. Description of the Related Art

Implantable medical devices such as implantable biosensors, breast implants, prostheses, surgical mesh implants, catheters, and neuromodulation leads, once implanted into a body, frequently induce an inflammatory reaction of the body. This common problem is called the foreign body response (FBR). In the first hours of the FBR, host macrophages are attracted to the surface of the implant. The macrophages arrive in sufficient numbers to spread over all surfaces of the implant that interface with the host tissue. When the surface of the device is smooth and impermeable to cells, these macrophages trigger a cascade of cytokines and chemokines that recruit fibroblasts and other extracellular matrix-building cells to the tissue adjacent to the implant. Typically, the end result of the FBR is the formation of a dense, fibrous, largely avascular capsule that partially or completely surrounds the device. This foreign body encapsulation can effectively isolate the implantable device from the surrounding tissue, physically, chemically, and electrically.

FBR limits the performance and operating lives of most implantable devices, which limitation is particularly debilitating in devices that are designed to continuously monitor or report data of measurements to an external data processing unit. For example, there have been many attempts to develop implantable devices that can continuously record blood glucose monitoring data; however, the FBR effects have frustrated these efforts. Similarly, proper functioning of neuromodulation electrodes and other electrostimulation devices is adversely affected by the FBR. Buildup of dense fibrous capsule tissue increases the electrical impedance from the electrodes to surrounding tissue and shortens the battery life.

Tissue implants used in cosmetic and reconstructive surgeries are another type of implantable devices, the functions of which can be adversely affected by the FBR. In particular, fibrous capsule can form and contract around the implant (e.g., breast implant), causing it to harden. The condition often requires the implant to be surgically removed. Barone F. E. et al., *Plast. Reconstr. Surg.* 90:77 (1992). Surgical trauma further increases the risk of capsular contracture, and the problem is most likely to occur in cases of reconstructive surgery. Henriksen T. F. et al., *Ann. Plast. Surg.* 54:343 (2005). Using open textured surfaces with roughness on the order of a pattern of 300 μm periodicity has significantly reduced the incidence of capsular contracture; however, the problem remains in 10 to 20% of all breast implant surgeries. Barnsley G P et al., *Plast. Reconstr. Surg.* 117:2182 (2006).

It has been shown that the biological response (e.g., FBR) to implanted biomaterials depends on the architecture of the biomaterial. Paul N. E. et al., *Biomaterials* 29:4056-64 (2008). In particular, porous biomaterials with pore sizes on the order of cellular dimensions have been shown to alter the FBR. For example, porous biomaterials with a pore size that is large enough to allow macrophage penetration was shown to increase vascularity in the capsule tissue. Brauker J. H. et al., *J. Biomed. Mater. Res.* 29:1517 (1995). Increased vascularity was shown to correlate with improved diffusion and plasma-exchange properties. Sharkawy A. A. et al., *J. Biomed. Mater. Res.*: 586 (1998). It was also recognized that a minimum pore size that allows colonization by host macrophages within the pore structure maximizes the density of new vessels within the scaffold, and elicits an FBR with significantly reduced capsule thickness than is seen when larger pore sizes, or pore sizes too small to permit cellular ingrowth, are used. Marshall A. J. et al., *Polymer Preprints* 45:100 (2004); Madden L. R. et al., *Proc. Nat. Acad. Sci.* 107(34):15211 (2010). These pore geometries have been shown to attract high concentrations of infiltrating macrophages. Marshall A. J. et al., supra; Tsai A., *Engineering biomaterial interfaces to control foreign body response: reducing giant cell formation and understanding host response to porous materials*, Ph.D. Dissertation, University of Washington (2007). It has been shown that the macrophages that colonize microporous structures or micro-textured surfaces assume an alternative phenotype that includes an altered cytokine release profile. For example, it has been shown that macrophages cultured on a micro-textured surface comprising an array of 10-μm diameter pillars separated by 20-μm spacing become activated and release both pro-inflammatory and anti-inflammatory cytokines Paul N. E. et al., supra. Further, evidence that porous materials promote angiogenic and anti-fibrotic activities has been found by measuring cytokine release profiles from tissues surrounding implants. Tsai A., supra.

Even when porous biomaterials are used in conjunction with medical devices, some degree of encapsulation still occurs. Rosengren, A. et al., *J. Biomed. Matl. Res.* 67a:918-926 (2003). Thus, the FBR remains a formidable problem for many types of implantable devices such as biosensors and tissue implants.

BRIEF SUMMARY

Disclosed herein are implantable devices coated with microporous surface layers with macrotopographic features that improve bio-integration at the interface of the implantable devices and the surrounding tissue.

One embodiment provides a microporous biomaterial with macrotopographic surface features, wherein substantially all the pores are each interconnected to at least 2 other pores, a mean diameter of the pores is between about 5 and about 100 micrometers, and any two adjacent pores are connected by a throat, a mean throat diameter of the throats being between about 5 micrometers and about 50 micrometers, and wherein the macrotopography is defined by a plurality of peaks and valleys, wherein each peak comprises a plurality of pores and has a height of between about 100 micrometers and about 2000 micrometers, and at least two adjacent peaks define a valley, the valley having a floor from which the heights of the adjacent peaks are measured.

In various embodiments, the microporous biomaterial comprises an open-cell structure throughout the entire microporous biomaterial; or the surface of the floor of the valleys between the peaks is impermeable to fluids; or the surface of the floor of the valleys between the peaks is microporous; or the biomaterial is permeable to fluids or electrolytes.

In various further embodiments, the mean pore diameter is between about 20 and about 40 micrometers, the height of each peak is between about 100 micrometers and about 500 micrometers, or between about 200 micrometers and about 1000 micrometers, or between about 500 micrometers and about 2000 micrometers, or between about 500 micrometers and about 1000 micrometers. In a further embodiment, the microporous biomaterial comprises an open-cell structure throughout the entire microporous biomaterial. In another embodiment, the biomaterial is biodegradable. In a further embodiment, the biomaterial is a hydrogel, silicone rubber, expanded fluoropolymer, a polymer or a metal. In various embodiments, the microporous biomaterial comprises a conductive polymer or metalized polymer, or the biomaterial has a thickness of at least 40 micrometers excluding the height of the peaks.

A further embodiment provides an implantable device comprising: a device body; and a microporous surface layer with macrotopographic features, wherein the microporous surface layer has continuously interconnecting pores, wherein substantially all the pores are each interconnected to at least 2 other pores, a mean diameter of the pores is between about 5 and about 100 micrometers, and any two adjacent pores are connected by a throat, a mean throat diameter of the throats being between about 5 micrometers and about 50 micrometers, and wherein the macrotopography is defined by a plurality of peaks and valleys, wherein each peak comprises a plurality of pores and has a height of between about 100 micrometers and about 2000 micrometers.

In various embodiments, the microporous surface layer of the implantable device has a thickness of at least 40 micrometers excluding the height of the peaks. In other embodiments, the mean pore diameter is between about 20 and about 40 micrometers. In various other embodiments, the height of each peak of the microporous surface is between about 100 micrometers and about 500 micrometers, between about 200 micrometers and about 1000 micrometers, between about 500 micrometers and about 2000 micrometers, or between about 500 micrometers and about 1000 micrometers. In a further embodiment, the implantable device further comprises an intermediate layer interposed between the device body and the microporous surface layer such as an adhesive layer or a conformal sheath that covers a part of or an entire native surface of the device body.

A further embodiment provides an implantable device comprising a device body; and a textured surface layer overlying the device body, wherein the textured surface layer comprises one or more granules of a microporous biomaterial, the granules forming a surface macrotopography that includes a plurality of peaks and valleys, each peak having a height of between about 100 micrometers and about 2000 micrometers, and wherein each granule comprises a plurality of interconnecting pores having a mean pore diameter of between about 5 and 100 micrometers, and any two adjacent pores are connected by a throat, a mean throat diameter of the throats being between 5 and 50 micrometers.

In various embodiments, the mean pore diameter is between about 20 and about 40 micrometers. In various other embodiments, the height of each peak of the microporous surface is between about 100 micrometers and about 500 micrometers, between about 200 micrometers and about 1000 micrometers, between about 500 micrometers and about 2000 micrometers, or between about 500 micrometers and about 1000 micrometers. In a further embodiment, the implantable device further comprises an intermediate layer interposed between the device body and the microporous surface layer such as an adhesive layer or a conformal sheath that covers a part of or an entire native surface of the device body. In various other embodiments, the granules cover the implantable device more than 80%, or more than 90% of a total area of a native surface of the device body.

A further embodiment provides a method for forming a microporous biomaterial with macrotopographic features:

(a) arranging macro-porogens to form a template for a dissolvable mold surface with macrotopographic mold features, wherein the macro-porogens have a mean macro-porogen diameter that is between about 100 and about 2000 micrometers;

(b) removing the macro-porogens from the mold surface of (a) by chemical dissolution;

(c) filling the macrotopographic mold features with micro-porogens such that points of contact and interstitial spaces between adjacent micro-porogens are formed, wherein the micro-porogens have a mean micro-porogen diameter that is between about 5 micrometers and about 100 micrometers;

(d) fusing the micro-porogens together at the points of contact;

(e) introducing a liquid biocompatible polymer precursor into the interstitial space between the micro-porogens;

(f) solidifying the biocompatible polymer precursor; and (g) removing the micro-porogens and the dissolvable mold surface.

In various embodiments, the macro-porogens comprise salt crystals, thermoplastic beads, poly(methyl methacrylate) or polystyrene beads. In other various embodiments, the micro-porogens comprise salt crystals, thermoplastic beads, poly(methyl methacrylate) or polystyrene beads. In further embodiments, the biomaterial is silicone rubber or hydrogel. In another embodiment, the dissolvable mold surface is poly (methyl methacrylate) or polystyrene.

A further embodiment provides a method comprising: implanting a microporous biomaterial with macrotopographic surface features, wherein the microporous biomaterial has continuously interconnecting pores, wherein substantially all the pores are each interconnected to at least 2 other pores, a mean diameter of the pores is between about 5 and about 100 micrometers, and any two adjacent pores are connected by a throat, a mean throat diameter of the throats being between about 5 micrometers and about 50 micrometers, and wherein the macrotopography is defined by a plurality of peaks and valleys, wherein each peak comprises a plurality of pores and has a height of between about 100 micrometers and about 2000 micrometers.

In a further embodiment, the microporous biomaterial is a surface layer overlying an implantable device.

A further embodiment provides a method comprising: implanting an implantable device comprising: a device body; and a microporous surface layer with macrotopographic features, wherein the microporous surface layer has continuously interconnecting pores, wherein substantially all the pores are each interconnected to at least 2 other pores, a mean diameter of the pores is between about 5 and about 100 micrometers, and any two adjacent pores are connected by a throat, a mean throat diameter of the throats being between about 5 micrometers and about 50 micrometers, and wherein the macrotopography is defined by a plurality of peaks and valleys, wherein each peak comprises a plurality of pores and has a height of between about 100 micrometers and about 2000 micrometers.

A further embodiment provides a method comprising: implanting an implantable device having a device body; and a textured surface layer overlying the device body, wherein the textured surface layer comprises one or more granules of a microporous biomaterial, the granules forming a surface macrotopography that includes a plurality of peaks and valleys, each peak having a height of between about 100 micrometers and about 2000 micrometers, and wherein each granule comprises a plurality of interconnecting pores having a mean pore diameter of between about 5 and 100 micrometers, and any two adjacent pores are connected by a throat, a mean throat diameter of the throats being between 5 and 50 micrometers.

BRIEF DESCRIPTION OF THE SEVERAL VIEWS OF THE DRAWINGS

FIG. 7 schematically illustrates a device with granules of different sizes attached to its surface. Panel A: Uniform size granules; Panel B: Mixture of granules having different sizes; Panel C: Mixture of two sizes of granules; Panel D: Granules of different sizes successively applied to the device.

DETAILED DESCRIPTION

Figure 1:
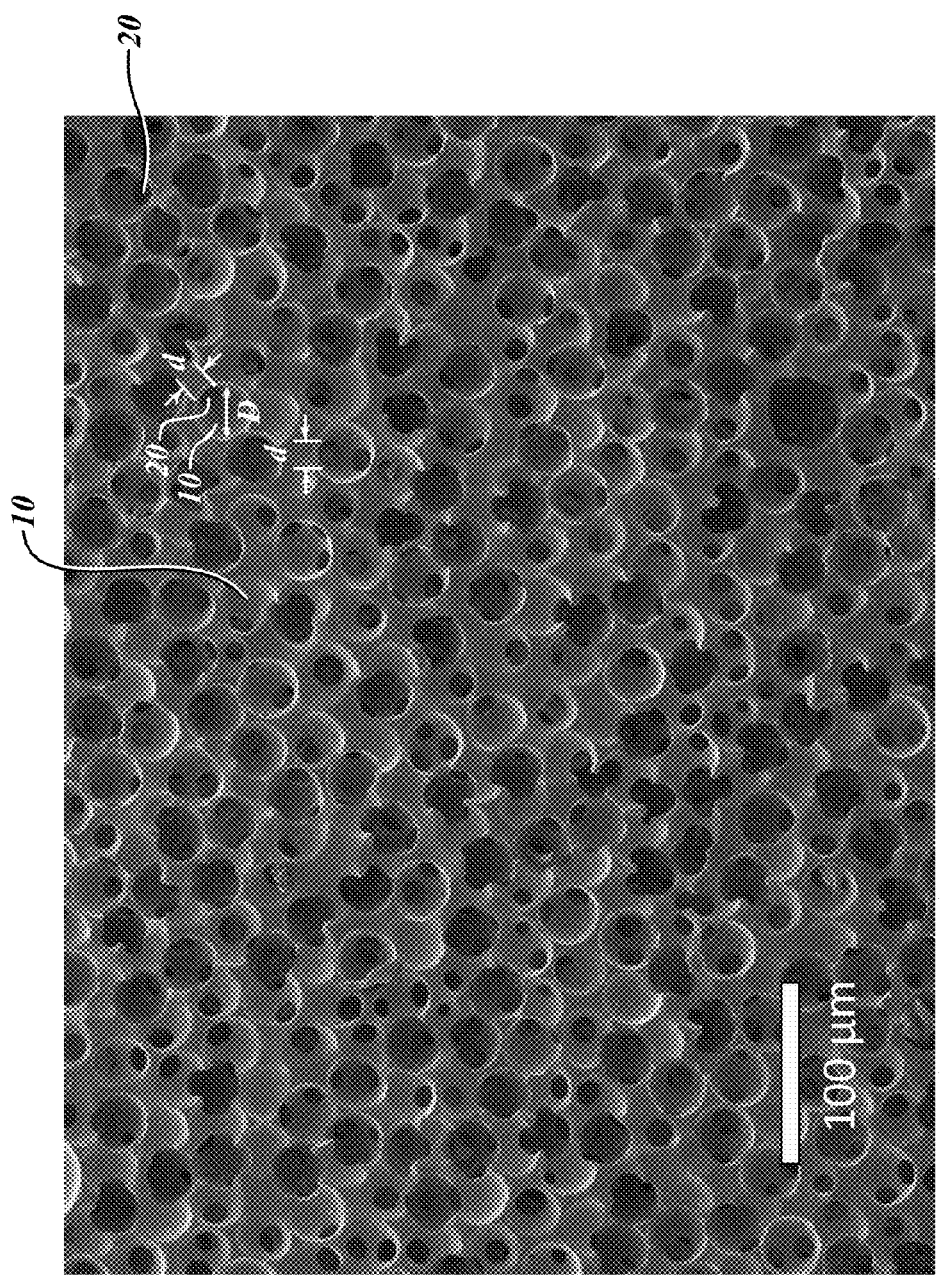
FIG. 1 is a Scanning Electron Micrograph (SEM) of microporous silicone scaffold with spherical pore diameter of about 30-35 micrometers and pore connections (throat) of about 12-14 micrometers in diameter.

The present disclosure is directed to implantable devices having microporous, textured surface layers, which serve to improve bio-integration at the interface between the implanted devices and the surrounding tissue. In particular embodiments, microporous surface layers that have textured or macrotopographic features are capable of minimizing or eliminating the FBR to the implanted device.

As used herein, "implantable devices" or "implanted device" refers to any type of medical device that is totally or partly introduced, surgically or medically, into the body of a subject (a human or an animal) or by medical intervention into a natural orifice, and which is intended to remain there after the procedure. An implantable device typically includes a device body and a surface layer. The device body carries out a particular function once implanted into the subject. Exemplary device bodies include, without limitation, soft tissue implants (e.g., breast implants, muscle prosthesis), implantable biosensors (e.g., glucose monitors), mass transfer devices (e.g., a drug infusing device), immunoisolation devices, electrostimulation devices, tissue expanders, tissue scaffolds (for supporting tissue growth), gastrointestinal liners, surgical mesh implants, and percutaneous devices (e.g., catheters, feeding tubes, and dialysis ports).

As used herein, "surface layer" or "coating layer" refers to a layer of microporous biomaterial overlying a native surface of the device body, the native surface being any part or all of the surface of the device body that, once implanted would be in direct contact with tissue but for the surface layer. As discussed in more detail herein, in certain embodiments the surface layer may be essentially a microporous tissue scaffold that facilitates the integration of the implanted device and its surrounding tissue, i.e., the tissue that is adjacent to the implanted device but outside of the micropores. In certain embodiments, the surface layer has macrotopographical features defined by peaks and valleys. In certain embodiments, the surface layer has a continuously open-pore or porous structure. In other embodiments, the surface layer comprises granular porous biomaterials that expose nonporous native surface of the underlying device, or an intermediate nonporous layer disposed between the underlying device and the surface layer.

"Microporous biomaterial" or "microporous scaffold" refers to a biocompatible material comprising an array of spherical or substantially spherical pores that are substantially connected. As used herein, "substantially connected" means that essentially every pore is connected to at least two, and preferably at least four other pores. Microporous scaffolds have been shown to allow tissue ingrowth and promote angiogenesis (e.g., formation of blood vessels). U.S. Application Publication No. 2008/0075752, which is incorporated herein by reference in its entirety, describes in detail the construction of a suitable microporous scaffold.

FIG. 1 shows a Scanning Electron Micrograph (SEM) of a porous silicone scaffold. Each pore 10 has a diameter "D." An opening caused by two pores partially fused into each other is called a throat (visualized as the dark "holes" 20 in FIG. 1). The throat also has a diameter "d." The diameter of a throat might range from infinitesimally small, when two pores are barely fused, to nearly the diameter of a pore, when two pores are almost completely fused. The microporous material may have a pre-determined pore diameter and throat diameter. In certain embodiments, the throat diameters (d) are approximately 15% to approximately 40% of the pore diameters (D) in order, according to non-limiting theory, to optimize the pro-angiogenic and anti-fibrotic properties of the microporous materials.

Typically, the mean pore diameter can be between 10 and 100 micrometers. The preferred pore diameter is between 20 and 40 micrometers, between 30 and 40 micrometers, between 25 and 35 micrometers, between 20 and 30 micrometers, or between 25 and 30 micrometers. Preferably, according to certain embodiments, the majority of the pores in the scaffold will be of such a preferred pore size. At these dimensions, the geometries of the pores may, according to non-limiting theory, constrain the invading macrophage cells and prevent them from spreading or aggregating into giant cells. The pore geometry thus may provide spatial cues that trigger the macrophages to secrete anti-fibrotic and pro-angiogenic factors.

Figure 2:
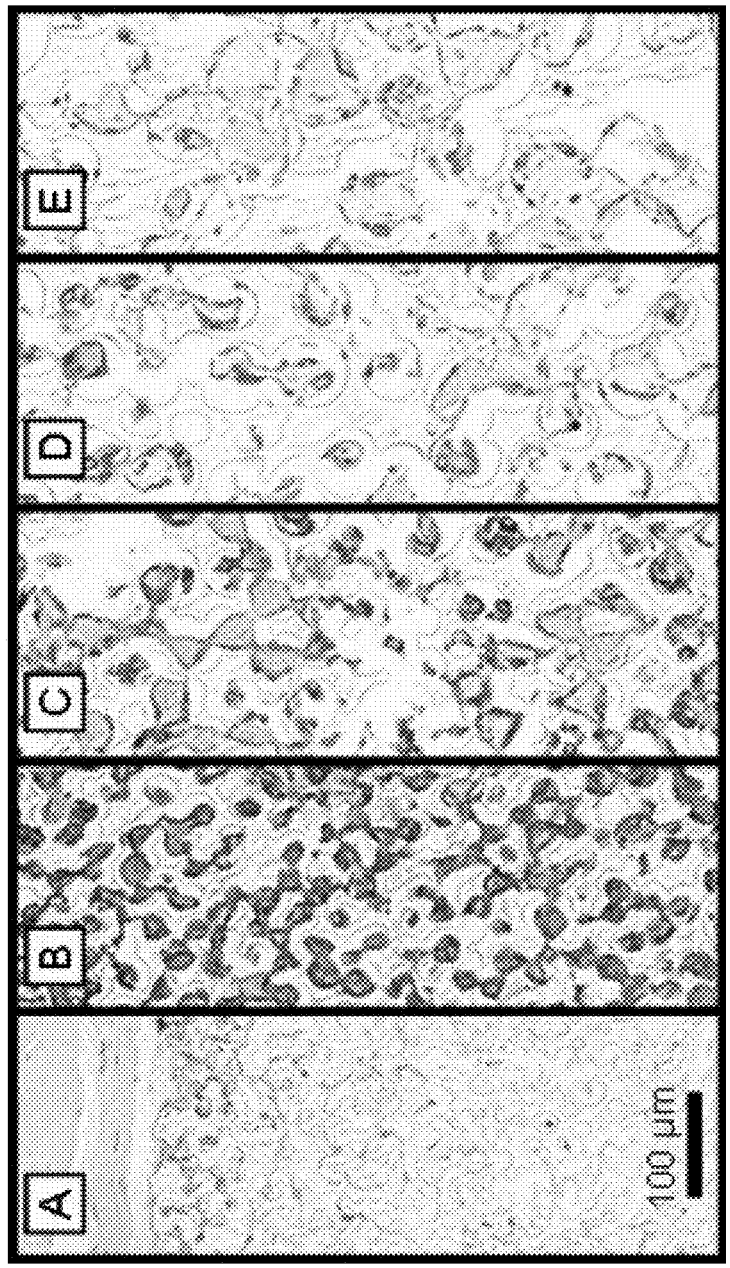
FIG. 2 shows tissue sections of sphere-templated microporous scaffolds of various pore diameters implanted subcutaneously in mice for 28 days; sections have been stained with BM8 macrophage marker. Pore sizes: (A) 20 micrometers; (B) 35 micrometers; (C) 50 micrometers; (D) 70 micrometers (E) 90 micrometers. The scaffold with 35-micrometer pores contains the highest concentration of macrophages.
Figure 3:
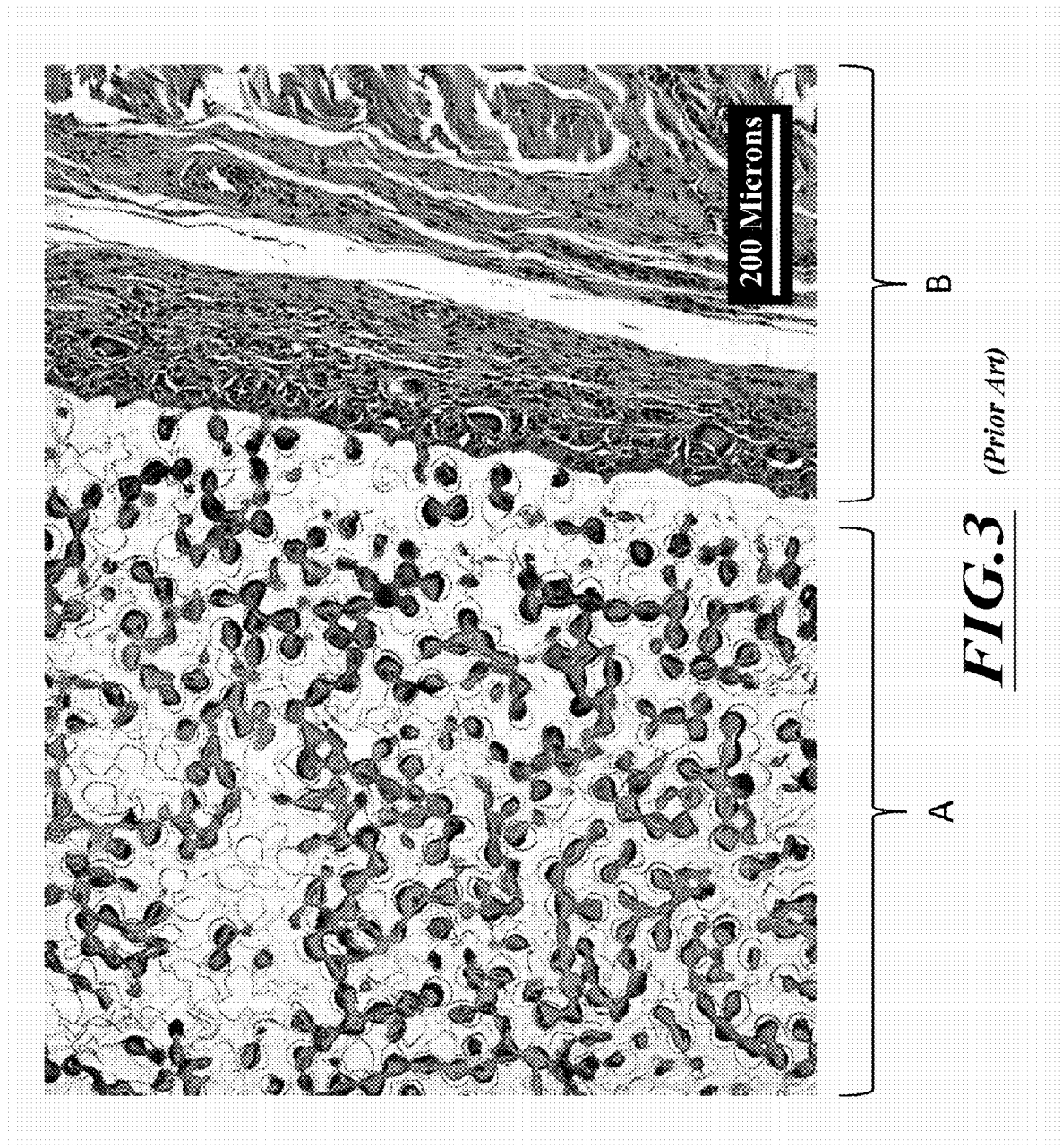
FIG. 3 shows tissue section of a microporous scaffold implanted subcutaneously into a pig for 28 days and stained with Hemotoxylin and Eosin. (A) Scaffold with stained cellular ingrowth into pores; (B) Surrounding tissue.

FIG. 2 shows scaffolds with substantially spherical pores in sizes of 20, 35, 50, 70, and 90 micrometers and with throat diameters 30% of respective pore diameters. As shown, the scaffold with 35 micrometer pore size is colonized with a higher concentration of macrophages than are the other porous scaffolds. FIG. 3 further shows a histological cross-section of a prior art microporous biomaterial displaying the interface with the surrounding tissue and the cellular ingrowth into the pores. As shown, the tissue at the material interface (e.g., leftmost area of panel B) is not densely fibrotic, but loose and vascular.

The mean diameter of the connection between the pores (i.e., throat) may in certain preferred embodiments be between 5 and 50 micrometers. The preferred diameter of the pore connections is between 8 and 25 micrometers, more preferably between 10 and 20 micrometers. Preferably, the majority of the pore connections will be of the preferred size. A macrophage cell diameter is typically about 10 to 15 micrometers in size, so the pore connections should be large enough to accommodate facile cell migration though the scaffold. Also, vascular endothelial capillaries are typically about 10 micrometers in diameter, so the scaffold should have pore connections large enough to permit ingrowth of a capillary network to support and nourish cells inside the scaffold.

In accordance with certain embodiments of this disclosure, when the microporous surface layer of the implantable device is textured and highly rough as compared to the native surface of the device body, the anti-fibrotic and pro-angiogenic effects of the microporous biomaterial can be amplified, which leads to an improved bio-integration between the implanted device and the surrounding tissue.

Textured Surface Comprising Granular Microporous Biomaterial

In certain embodiments, a monolayer of the microporous biomaterial in granular form provides textured surface features, which features are also interchangeably referred to as "macrotexture" or "macrotopography."

Figure 4:
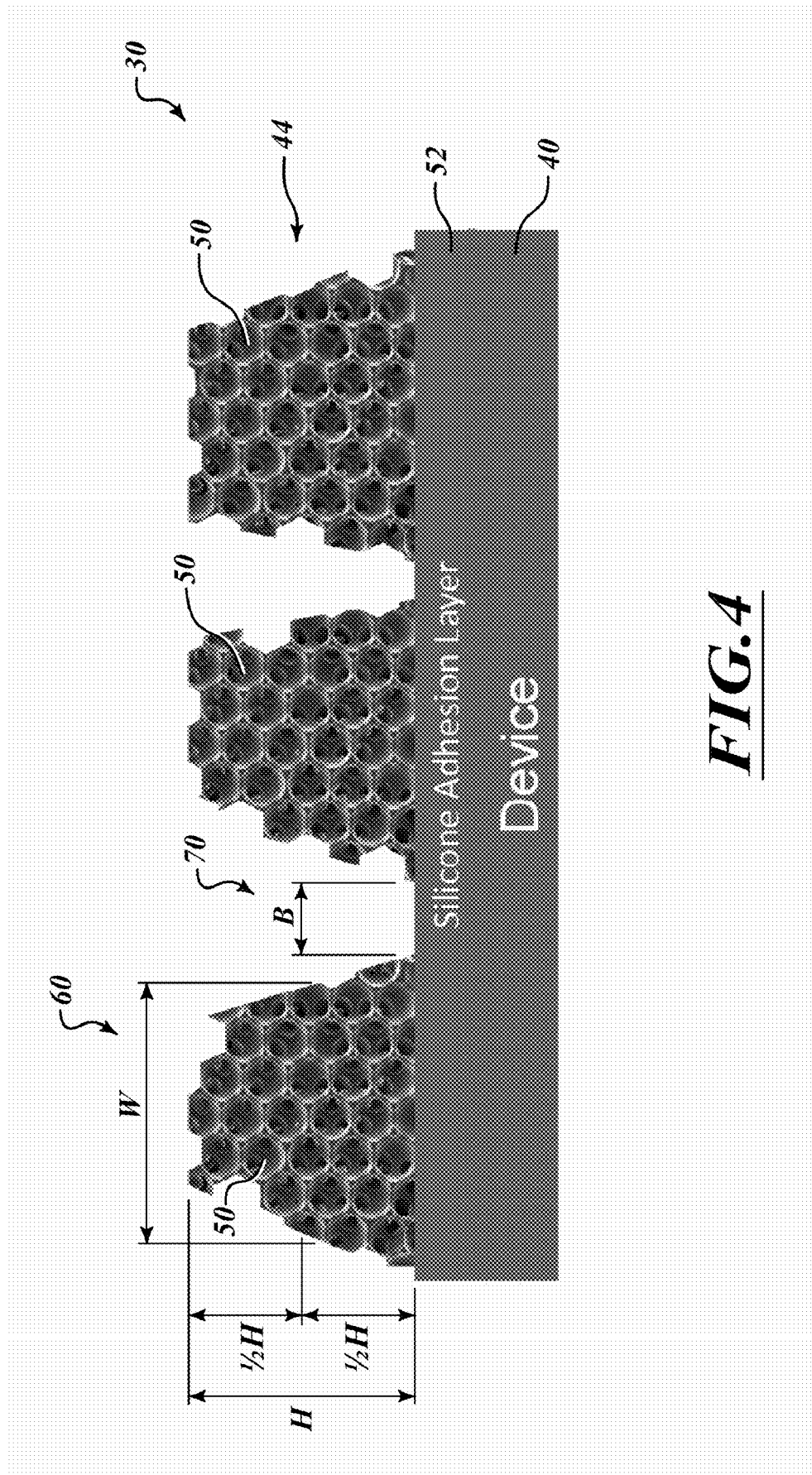
FIG. 4 schematically shows a cross-sectional view of an embodiment of the present disclosure, in which a device is covered with a microporous surface layer having macrotopographic features formed by granules of a microporous biomaterial.

FIG. 4 shows schematically one configuration of an implantable device 30 that comprises a device body 40, and a layer 44 of granules 50 of a microporous biomaterial positioned thereupon. Also shown in FIG. 4 is an optional intermediate layer 44 (e.g., a silicone adhesive layer) interposed between the device body 40 and the monolayer 44.

The granules define a surface macrotopography that include peaks 60 and valleys 70. The peaks and valleys correlate to the sizes of the granules and the space therebetween, respectively. More specially, a peak represents a projection or protrusion in the surface macrotopography, whereas a valley represents a depression in the surface macrotopography and is a space defined by two or more adjacent peaks. In certain embodiments, the surface density or coverage by the porous granules may be controlled such that the floor of the valley is an exposed portion of the surface of the underlying device body or an exposed portion of an intermediate layer (e.g., an adhesive layer). In these embodiments, the macrotextured surface is intermittently porous, in other words, the floors of at least some valleys are non-porous surfaces (see also, FIG. 5)

The height ("H") of the peak is typically measured relative to the floor of the adjacent valley (e.g., the surface uncovered by the granule). The width of the peak ("W") is defined as the dimension at half height and is orthogonal to the height of the peak. A dimension of the valley can be characterized by breadth ("B"), which is the shortest distance at the floor of the valley between any two peaks that define the valley.

Thus, one embodiment provides an implantable device comprising: a device body; and a textured surface layer overlying the device body, wherein the textured surface layer comprises one or more granules of a microporous biomaterial, the granules forming a surface macrotopography that includes a plurality of peaks and valleys, each peak having a height of between about 100 micrometers and about 2000 micrometers, and wherein each granule comprises a plurality of interconnecting pores having a mean pore diameter of between about 5 and 100 micrometers, and any two adjacent pores are connected by a throat, a mean throat diameter of the throats being between 5 and 50 micrometers, and at least two adjacent peaks define a valley, the valley having a floor from which the heights of the adjacent peaks are measured.

As used herein, "about" refers to a range of values ±20% of a specified value. For example, the phrase "about 100 micrometers" includes a range of ±20% of 100 micrometers, namely, 80 to 120 micrometers.

In various further embodiments, the peaks have heights between about 200 micrometers and about 1000 micrometers, between about 500 micrometers and about 2000 micrometers, or between about 500 micrometers and about 1000 micrometers.

In various further embodiments, the interconnecting pores have a mean pore diameter of at least about 10 μm and not more than about 90 μm. In some embodiments, the range of diameters of porogens is less, e.g., from about 20 μm to about 75 μm, from about 20 μm to about 30 μm, from about 30 μm to about 60 μm, or from about 30 μm to about 40 μm.

Figure 5:
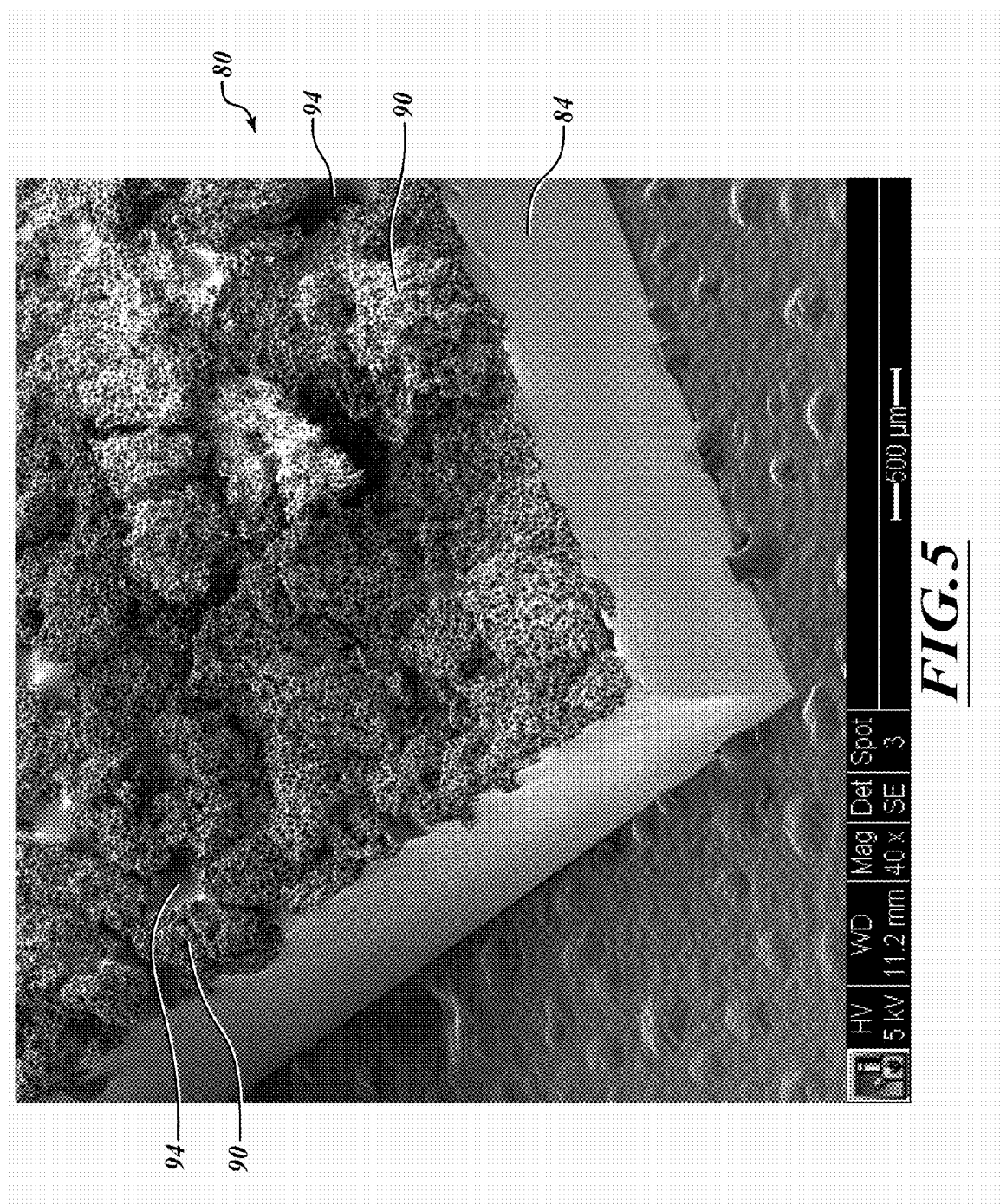
FIG. 5 shows an SEM of a monolayer of 300-500 micrometer granules of microporous silicone adhered to solid silicone.

In certain embodiments, the granules are distributed in a single layer (i.e., a monolayer). FIG. 5 is an SEM of an implantable device 80 comprising a solid silicone layer 84 and a monolayer surface of adhered granules of 300-500 micrometers formed of sphere-templated microporous silicone. The macrotopography of the monolayer surface is defined by peaks 90 and valleys 94 (with exposed nonporous surface at the floor).

Upon implantation into tissue, the entire internal surface area of the interconnecting pores of the microporous surface layer may over time become covered by host macrophages. By providing a high concentration of bioavailable surface area, these microporous tissue scaffolds encourage ingrowth of host macrophages, and release by these cells of clinically desirable factors such as anti-fibrotic and pro-angiogenic factors. In cases where the scaffold pore size can be matched to the approximate size of the macrophages, the bioavailable surface area may be maximized, which in turn results in a maximum local concentration of macrophages on the internal surface of the scaffold. If the microporous biomaterial is at least several pore layers thick, then the local concentration of these beneficial factors may vary as a function of the concentration of the surface pores that are in direct contact with the surrounding tissue. By incorporating macrotopographic features as described herein, the concentration of "surface pores" can be more than doubled and the availability of such factors amplified, relative to non-textured microporous surfaces. As used herein, "surface pores" refers to the outermost layer of pores within a microporous surface layer of an implantable device. When the implantable device is implanted, the surface pores are directly exposed to the surrounding tissue. Thus, the term "surrounding tissue" also includes tissue that grows into the spaces between the macrotopographic features of the microporous biomaterial.

Figure 6:
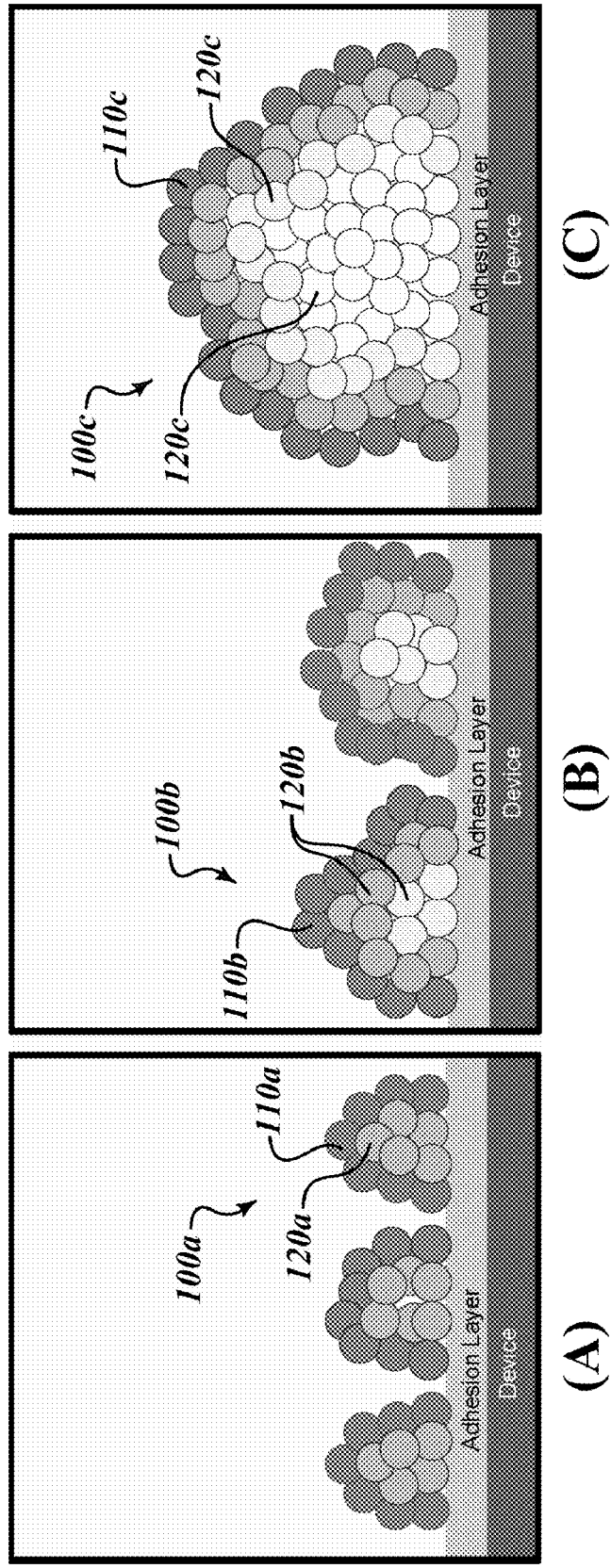
FIG. 6A-C schematically illustrates the effect of the granule size on the concentration of surface pores that are directly exposed to adjacent tissue.

For macrotopographic features defined by peaks of a given shape, the total number of surface pores is independent of the size of the peaks. However, the height of the tissue interface layer is proportional to the size of the peaks. The term "tissue interface layer" as used herein refers to the tissue layer that includes both the tissue that grows into the pores within the peaks as well as the tissue that grows into the spaces between the peaks. The tissue interface layer does not include the portion of the surrounding tissue that is beyond the height of the peaks. Thus the concentration of surface pores per unit volume within the tissue interface layer is higher for smaller peaks than for larger ones. As schematically shown in FIG. 6, individual granules 100a, 100b and 100c are in an ascending order of sizes, which correlate to a descending order of the surface concentrations of surface pores 110a, 110b and 110c. The numbers of the interior pores (120a, 120b and 120c), which have less involvement in reducing the FBR, increase as the size of the granules increases. Such correlation between the granule size and surface concentration of surface pores may favor the use of smaller granules according to certain embodiments described herein. However, if the peaks are too small (e.g., smaller than 100 micrometers), there may not be enough total pores to accommodate a large enough reservoir of macrophages, such that from the present disclosure the skilled person will appreciate that selection of an appropriate dimension may vary depending on the particular microporous scaffold.

Surface pore concentration per unit projected area (i.e., a 2-D area projected from 3-D object such as a peak) is influenced by the height-to-width ratio of the granule or the peak. Typically, the greater the height-to-width ratio of the peaks (e.g., the granules) that define the macrotopographic features, the greater the concentration of surface pores per unit projected area. In certain embodiments, the height-to-width ratio of the peaks that comprise the macrotopographic features should be greater than 1:2, more preferably greater than 1:1, and most preferably greater than 2:1.

Thus, the shape and/or size of the valley in the surface macrotopography potentially play a role in amplifying the effects of pro-angiogenic and anti-fibrotic factors. As these factors are released into the valleys between peaks, their diffusion into the tissue can be slowed down by the confining geometry. For example, when the breadths of the valleys are narrow enough to create "coves," which are valleys that have breadths equal to or less than the width of the peaks surrounding the valleys, the favorable factors released from the surface pores of the neighboring peaks can accumulate and remain in the vicinity of the interface longer, compounding the amplification of their effects.

In certain embodiments, the microporous surface layer can be further characterized by packing density or surface coverage (in percentage) of granules on a native surface of the device body. In applications in which an intermediate layer is employed (e.g., a conformal adhesive layer or a sheath), for purpose of estimating the surface coverage, the intermediate layer is treated as if it is a native surface of the device body. For example, in a surface monolayer, each granule may or may not be in contact with several other granules. The packing density of a layer of granules on the surface can be increased by applying successively smaller size fractions of granules in separate steps. "Size fraction" refers to a population of granules of substantially the same size obtained, for example, by size sorting such as sieving. When the granules are applied in this way, smaller granules are available to fill the spaces between the larger granules as shown in FIG. 7. The granules may be substantially uniform sized or a mixture of different sizes. When granules are of uniform size, approximately 65% of the surface is covered (FIG. 7, panel A). By using a mixture of sizes, slightly more coverage is achieved (FIG. 7, panel B). Even more coverage is obtained by using two different sizes of granules (about 80% coverage, FIG. 7, panel C). The most coverage—about 90%—is achieved by successive application of granules starting with the largest size and then applying the next smaller size and so on (FIG. 7, panel D).

Thus, various embodiments describe implantable devices in which the granules cover more than 80%, or more than 90% of a total area of the surface of the implantable device.

Advantageously, implantable devices with textured, granular surface layers can be fabricated by applying (e.g., sprinkling and adhering) granules to the surface of device bodies, especially those of large and/or irregular shapes. Thus, devices such as breast implants and percutaneous devices, where minimizing of the foreign body capsule is needed but mass transfer through the pores of the scaffold is not required, are well-suited for the direct application the granules for forming a macrotextured surface that interfaces with the surrounding tissue. In particular, biosensors (such as glucose sensors), glaucoma drainage implants, immunoisolation devices (such as devices containing pancreatic islet cells), intraarterial shunts, and catheters or other percutaneous access devices can benefit from the reduction of capsule thickness. The reduction of capsule thickness also helps to increase infection resistance, because host antimicrobial cells have more facile access to the surface of the device without needing to cross the transport barrier created by a thick dense capsule.

Thus, in some embodiments, while the surfaces that define the tops and sides of the peaks are microporous, the surfaces of the bottoms of the valleys (i.e., valley floors) comprise exposed portions of the native surface of the device body that are non-porous and impermeable to cells. In some embodiments, the microporous biomaterial is connected to a nonporous intermediate layer impermeable to cells.

Figure 13:
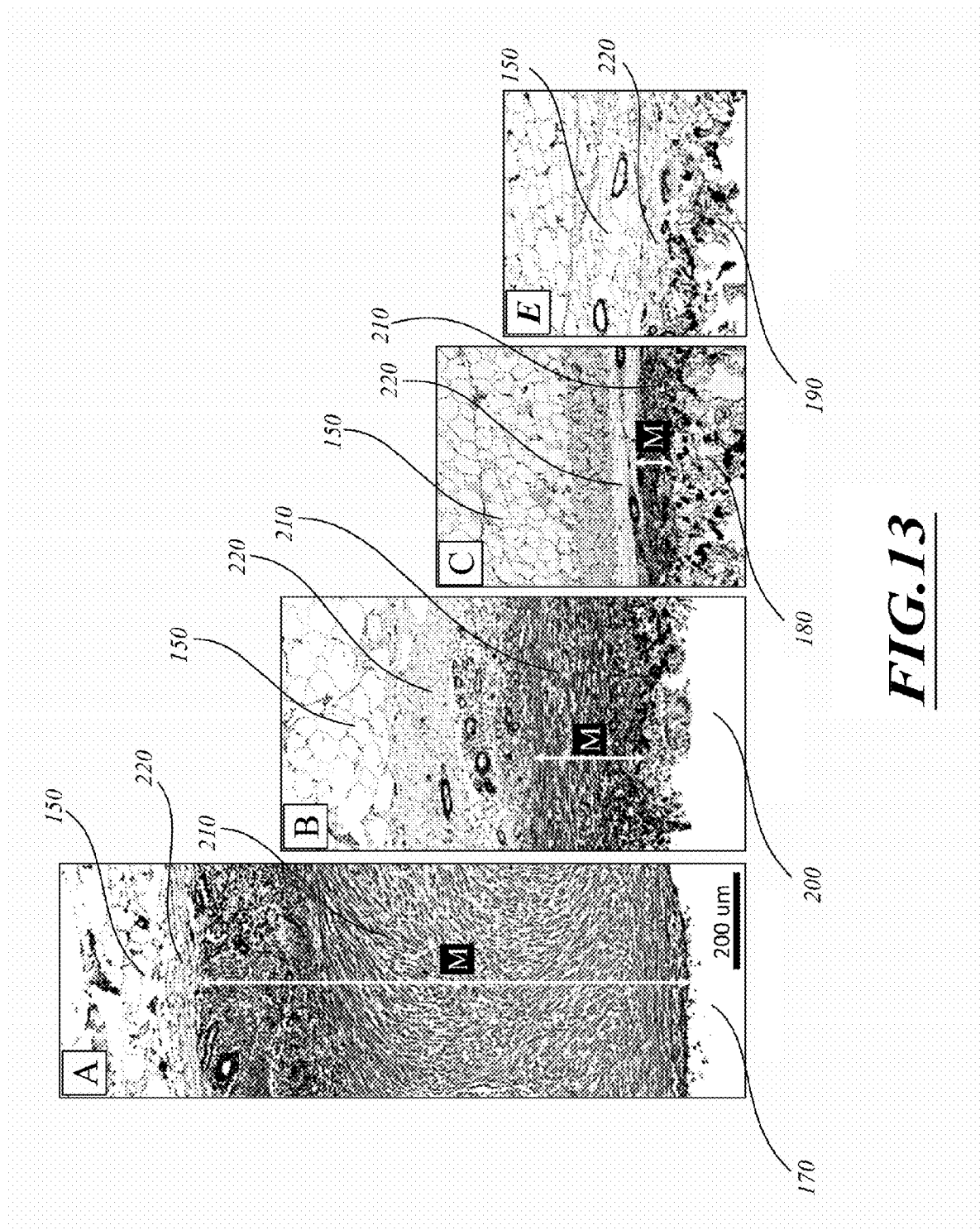
FIG. 13 shows alpha smooth muscle actin stained histological sections of the tissue-implant interfaces for four biomaterial surface geometry configurations. The relative thicknesses of the myofibroblast layer of the capsule are compared. Panel A: Smooth nonporous silicone; Panel B: Textured silicone; Panel C: Silicone with 27-micron pore size; and Panel E: Macrotextured microporous silicone in accordance with an embodiment of the present disclosure.

As discussed, macrotextured microporous surface is particularly advantageous for reducing the thickness and density of the foreign body capsule. It is hypothesized that the peaks and valleys that define the macrotopography of the microporous biomaterial surface layer interfere with lattice contraction, complementing the vascularized interface by relieving stresses from collagen lattice contraction that normally exacerbate fibrotic buildup. FIG. 13 shows that alpha smooth muscle actin ($\alpha$-SMA)-positive myofibroblasts—the stress elements that are a hallmark of capsule scar tissue—are absent in the foreign body response to the microporous macrotextured biomaterial (E), suggesting a stress-relaxed condition.

Figure 14:
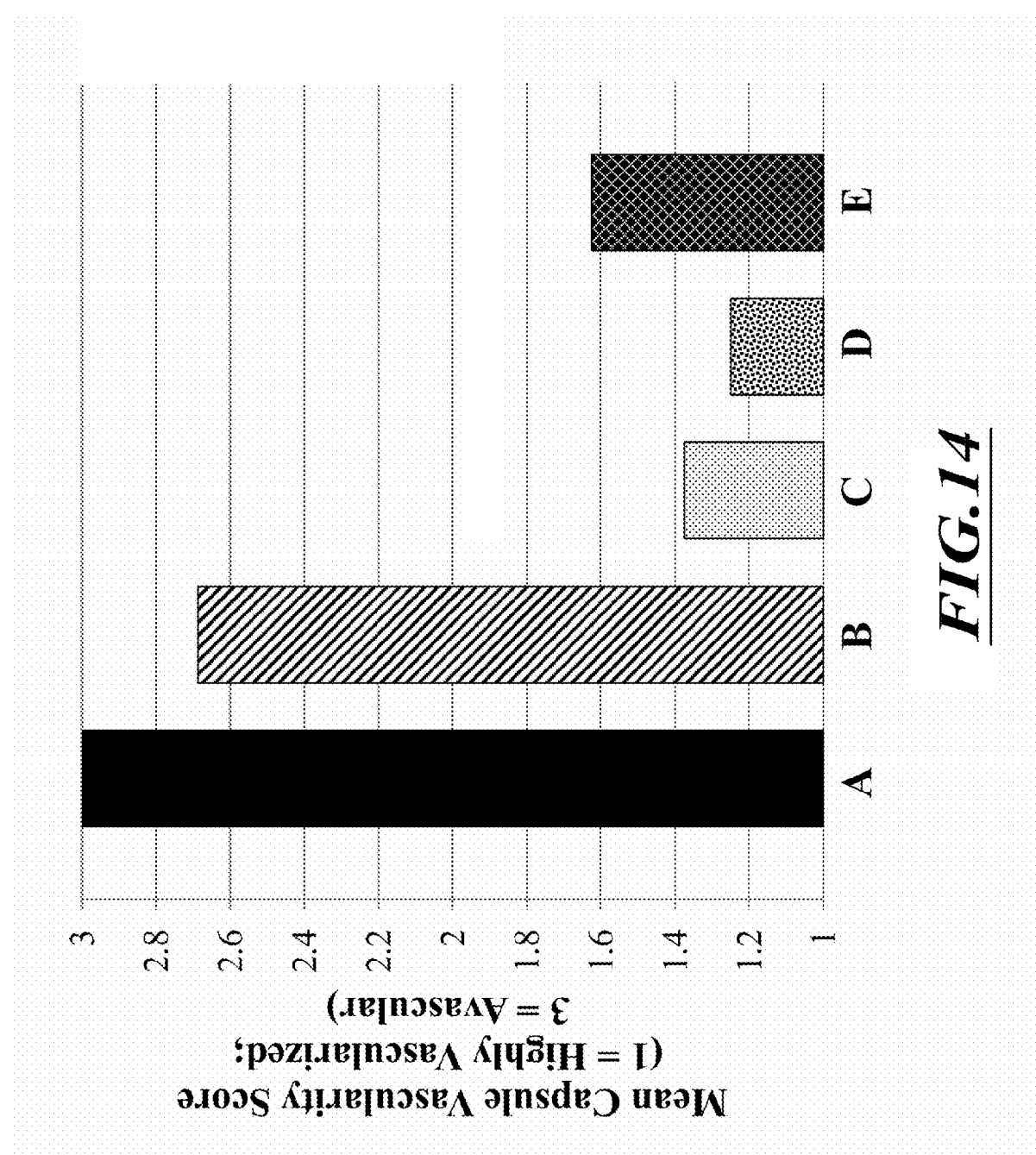
FIG. 14 is a column chart comparing the measured mean capsule vascularity scores after implanting silicone biomaterials with five different surface geometry configurations. Column A: smooth nonporous surface; Column B: textured nonporous surface; Column C: 27-micron porous surface; Column D: macrotextured and continuously microporous surface; and Column E: macrotextured and intermittently microporous surface.

Unexpectedly, a textured surface with intermittently nonporous valley floors is shown to be even more effective in capsule reduction than a continuously porous macrotextured surface (see, e.g., Example 4). It is hypothesized that, while the peaks and valleys that define the macrotopography interfere with lattice contraction and complement the vascularized interface, the intermittent nonporous surface at the valley floor manages the degree of vascularization by avoiding hyper-vascularization within the valley that may otherwise fill the valley and diminish the effective height of the macro-topographical features (peaks). FIG. 14 shows the vascularity scores of a number of surface geometries (see, also, Example 4). As shown, macrotextured continuously porous surface (D) has the highest degree of vascularization. The macrotextured intermittently porous surface (E) has a lower degree of vascularization as compared to (D) as well as (C), which is a continuously porous but non-textured surface; but a higher degree of vascularity as compared to nonporous surfaces (A) and (B). Thus, it is demonstrated that the textured surface with intermittently nonporous valley floors is capable of managing the degree of vascularity, thereby maximizing the benefits of the microporosity and the surface macrotopography.

Figure 15:
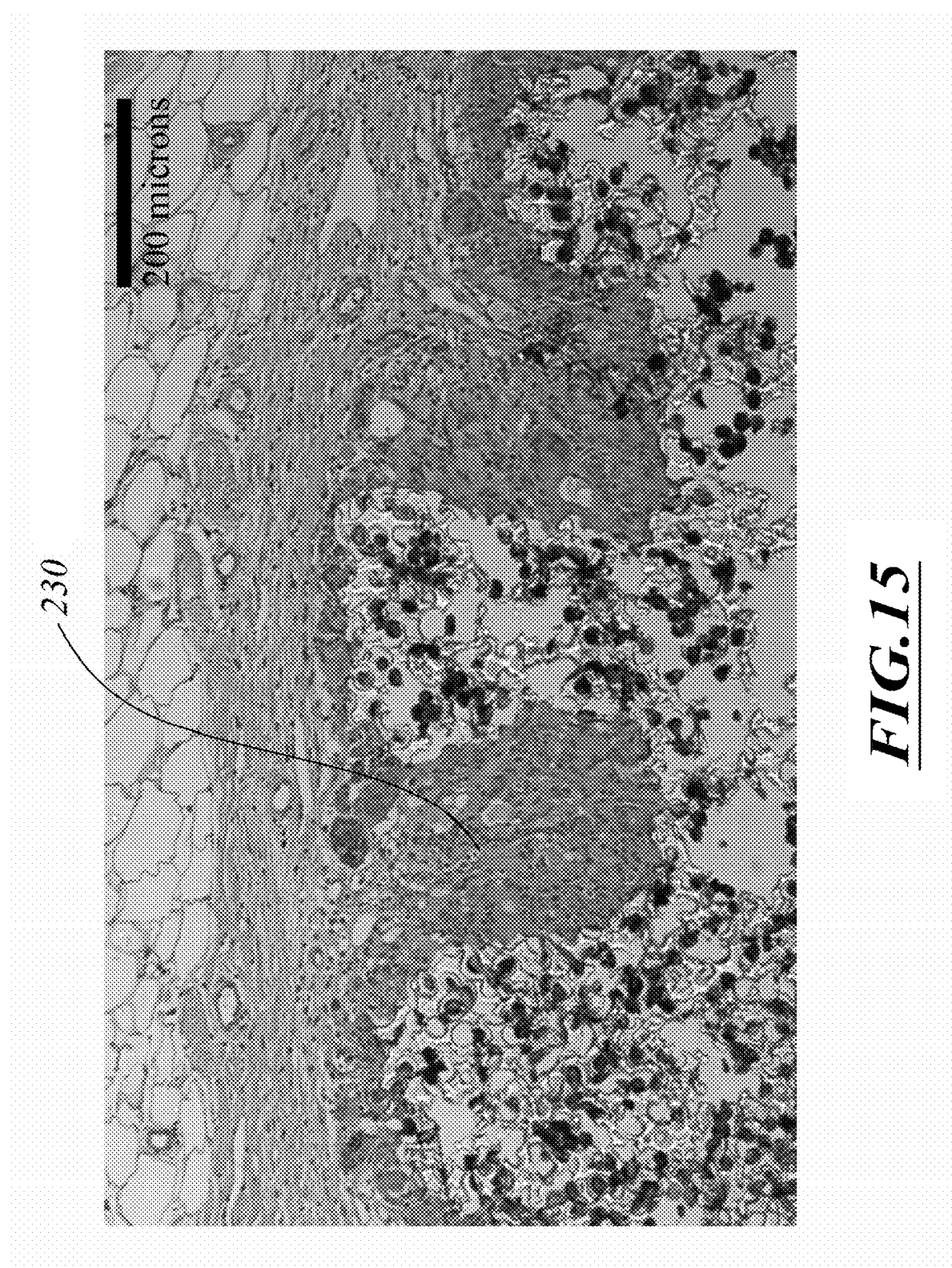
FIG. 15 shows a Hemotoxylin and Eosin stained histological section of the tissue implant interface for a macrotextured biomaterial with continuously microporous surfaces; the surfaces of peaks and the floors of the valleys between the peaks are porous with 27-micron diameter spherical pores to allow vascularized tissue ingrowth.

FIG. 15 shows that, in a continuously porous macrotextured surface (D), highly vascularized tissue 230 fills the valley between peaks, thereby diminishing the effective height of the macrotopographical features.

Figure 8:
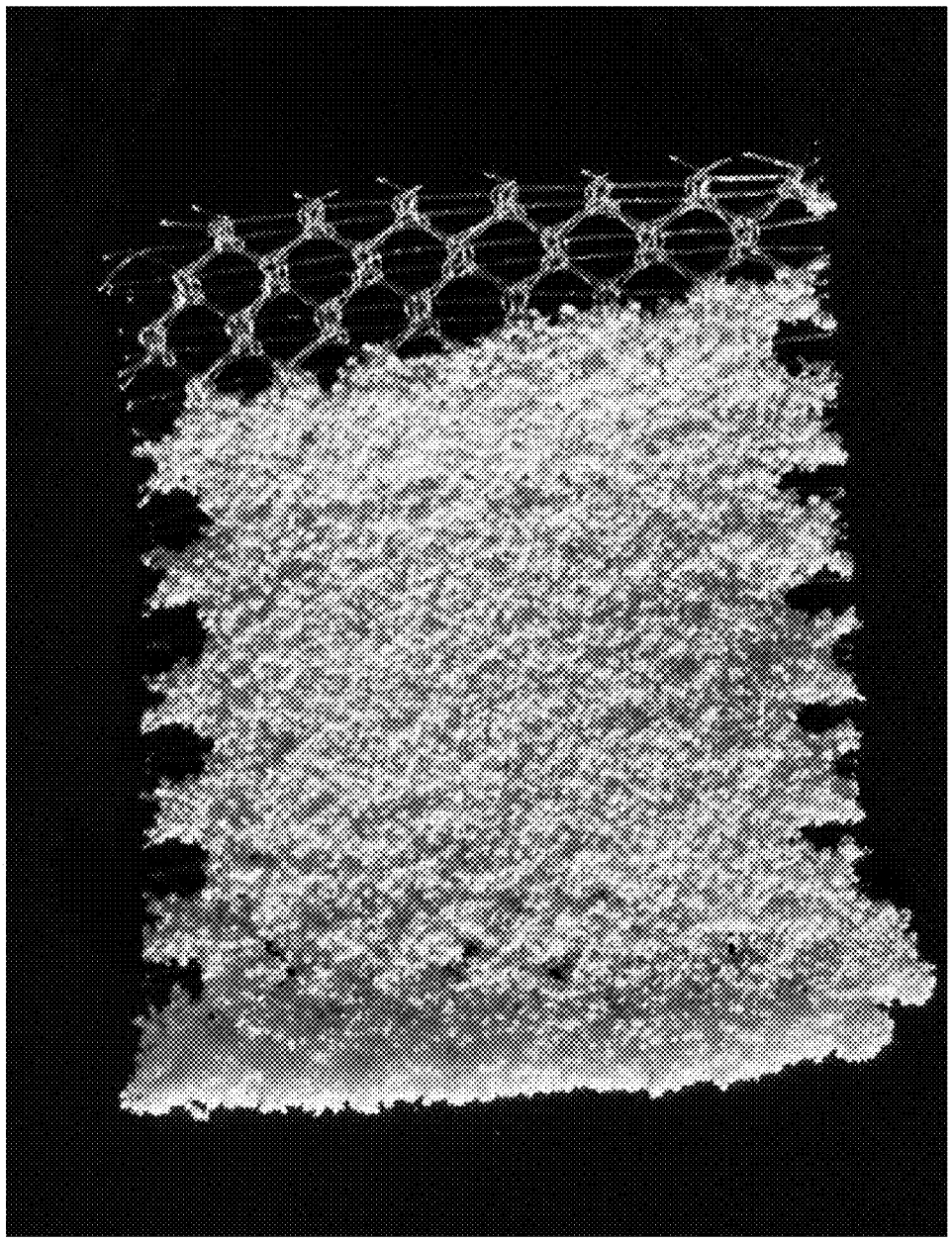
FIG. 8 shows a hernia repair mesh (polypropylene) with mesh fibers coated with adherent monolayer of 300-500-micrometer granules of microporous silicone.

A further example of this mode of application is shown in FIG. 8, in which a polypropylene mesh for surgical hernia repair coated or dusted with porous granules that adhere to the surface of the mesh. The coated mesh may have varying degrees of coverage. For example, in a preferred embodiment, the porous granules coat only the mesh filaments such that the original openings between the mesh filaments are substantially exposed.

The elements of the disclosed embodiments are described in further detail below.

1. Microporous Biomaterial

Implementations of porous biocompatible materials have been shown to allow ingrowth of tissue, and especially of blood vessels. U.S. Application Publication No. 2008/0075752, the disclosure of which is incorporated in its entirety. Numerous criteria exist for assessing angiogenesis and fibrosis in vivo and in vitro and will be known to persons familiar with the relevant art. E.g., Oates et al., *Biomaterials* 28:3679 (2007); Rosengren et al., *J Biomed Mater Res* 67A: 918 (2003).

A variety of materials and methodologies are known for the production of a porous biocompatible material and may be adapted to produce the microporous biomaterial with pores of specific geometries and sizes. Templates for the pore formation are referred to as "porogens." For certain microporous biomaterial, the porogens are also referred to as "microporogens," which are sized so that a sphere of the same volume has a diameter ranging from about 5 micrometers to about 100 micrometers.

Briefly, and by way of non-limiting example, microporous biocompatible materials may be made by (1) sintering or fusing (partially or fully) an array of micro-porogens, (2) casting a biocompatible material into the spaces among fused porogens and then (3) dissolving away, evaporating or otherwise removing the porogens to yield a network of interconnected voids (pores). The partially fused or sintered porogens form what will be the interconnecting throats of the porous material. It is generally most convenient to prepare sintered porogens in a mold. The size of the mold may be any size that is larger than the intended size of granules. A convenient mold size is about 5 cc to 10 cc in volume, e.g., about 3 cm×2 cm×1 cm.

Although porogens may be any shape (e.g., spherical, cubic, polyhedrons such as dodecahedrons, ellipsoids, cylindrical, irregular), generally porogens are spherical or nearly spherical in shape. Spherical shapes can be efficiently, tightly packed together while still retaining controlled spaces between the porogens, resulting in a highly interconnected network of pores.

The porogens may vary in size. However, their sizes are generally controlled and at least a majority, and more typically, substantially all of the porogens have a diameter that is at least about 10 µm and not more than about 90 µm. In some circumstances, the range of diameters of porogens is less, e.g., from about 20 µm to about 75 µm, from about 20 µm to about 30 µm, from about 30 µm to about 60 µm, or from about 30 µm to about 40 µm, e.g., about 31, 32, 33, 34, 35, 36, 37, 38, 39, 40, 41, 42, 43, 44, 45, 46, 47, 48, 49 or 50 µm. Size can be controlled by any number of ways. For example, porogens can be sized by sieving or by the manufacturing method used to generate them. In some circumstances, substantially all the porogens have a similar diameter. As used herein, the term "substantially all the porogens" refers to the percentage of porogens within one standard deviation on either side from the mean diameter, within two standard deviations on either side, or within three standard deviations on either side. The term "diameter of a porogen" refers to the longest line segment that can be drawn that connects two points within the pore, regardless of whether the line passes outside the boundary of the pore. In preferred embodiments, the porogens are monodisperse, i.e., the porogens have substantially the same diameters and the difference in the diameters of any two porogens is no more than 20% of the larger diameter.

Porogens may be manufactured from a variety of materials. Generally, the material will in certain embodiments be hard and rigid enough to withstand grinding. Many suitable materials are known for such use and may vary depending on the selected biocompatible material in which pore formation is desired, and on the fabrication process that is employed. One such material is polymethylmethacrylate (PMMA). Other examples of suitable hard materials for use as porogens include metals, composites and ceramics. In addition to its hardness, the material needs to be extractable from the biocompatible material forming the scaffold. Chemical extraction using acetone, dichloromethane or other suitable solvent is typically used, although physical methods that selectively remove porogens (e.g., by application of heat and/or pressure) may also be used. At times, extraction conditions may involve both chemicals and physical parameters (e.g., temperature, elevated pressure, or reduced pressure).

The shape and diameter of a pore typically may reflect the shape and diameter of a given porogen. In certain embodiments, the pores may be slightly smaller or larger (e.g., ±1-10% volume) than the loose porogens before they are arrayed and sintered due, in part, to the potential shrinking or swelling of the biomaterial following the removal of the porogens. The diameter and shape of the pores, as well as the connections between them may be assessed using scanning electron microscopy (see, e.g., FIG. 1).

Generally, in certain embodiments described herein the diameters of throats (or throat diameter) resulting from packed and fused porogens is between about 15% to about 40% of the mean diameter of the porogens. As used herein, "throat diameter" refers to the diameter of the cross-section of the connection between two pores in the plane normal to the line connecting the centroids of the two pores (if pores had uniform mass), where the plane is chosen so that the area of the cross-section of the connection is at its minimum value.

In addition, packing usually places each porogen in contact with about four to about twelve other porogens. The packed porogen array and the resulting porous biocompatible scaffold which is formed around the porogens can be any thickness and, in certain embodiments described herein, is usually at least 70 μm or most often at least 100 μm. The biocompatible material is typically a polymer or any of a number of other biocompatible materials known to the art that are capable of being formed into granules having volumetric and pore dimensions as described herein, and also being capable of maintaining such dimensions when exposed to biochemical and physicochemical forces of the physiological milieu following introduction in vivo. A typical polymer thus may comprise any biocompatible polymer, such as synthetic polymers, naturally-occurring polymers, or mixtures thereof. Exemplary synthetic biocompatible polymers include, but are not limited to, 2-hydroxyethyl methacrylate (HEMA), silicone such as Nusil MED-6215, Nusil MED-4830, or other silicone suitable for implantation, poly(epsilon-caprolactone)dimethylacrylate, polysulfone, (poly)methyl methacrylate (PMMA), soluble Teflon-AF, poly ethylene teraphthalate (PET, Dacron), Nylon, polyvinyl alcohol, polyurethane, hydroxyapatite, and mixtures thereof. Exemplary naturally-occurring biocompatible polymers include, but are not limited to, fibrous or globular proteins, complex carbohydrates, glycosaminoglycans, connective tissue extracellular matrix (ECM) components, such as collagen or fibrin, or mixtures thereof. Thus, the polymer scaffold may include collagens of all types, elastin, laminin, hyaluronic acid, alginic acid, desmin, versican, matricellular proteins such as SPARC (osteonectin), osteopontin, thrombospondin 1 and 2, fibrin, fibronectin, vitronectin, albumin, etc. Natural polymers may be used as substantial components of the scaffold or as additives to improve the biocompatibility of a scaffold that comprises a synthetic polymer. Other biocompatible materials suitable for forming the porous biomaterial scaffold may include hydroxyapatite and a variety of biocompatible metals including but not restricted to titanium. Further exemplary biocompatible materials can be found in, e.g., U.S. Application Publication Nos. 2009/0012625 and 2008/0200430, which are incorporated herein by reference in their entireties.

Optionally, the biocompatible material may in certain embodiments be degradable or bioresorbable. Degradation may occur via natural processes such as in vivo metabolic pathways, or by hydrolysis or following treatment with, e.g., an enzyme or chemical that acts upon the biocompatible material. For example, the biocompatible material may comprise crosslinked hyaluronic acid and may be degraded by hyaluronidase. Other suitable biodegradable materials include fibrin and collagen. For some applications, it may be desirable to use granules comprising combinations of biodegradable materials that degrade at different rates.

The biocompatible material may in certain embodiments possess bioactivity due to incorporation into the material of a biologically active ingredient, or may be made partially or solely of a bioactive substance, such as salicylic acid, or of a substance that responds to electrical stimulation, such as polyaminoarenes. The biocompatible material may also be composed partially or solely of an electrically conducting polymer, or the surface of the biomaterial may be metalized.

2. Granules of Microporous Biomaterial

As described herein, granules may be applied to a surface of the device body to provide surface topographic features, including peaks and valleys. In certain embodiments, granules of porous biocompatible material may comprise pieces of a larger material. In one simple implementation, for example, a biocompatible material—before porogens are extracted—may be mechanically broken into smaller pieces by grinding, shattering, shearing, sonicating, or the like, to obtain granules. Granules of a desired size can be selected from the resultant population of granules.

Many different tools and machines are readily available that may be used for making granules, as will be recognized by persons of skill in the art based on the disclosure herein, and as may vary as a function of the particular biocompatible materials and/or porogens that are used. For example, a coffee grinder is a suitable machine. Other suitable devices include blenders, crushers, sonicators, hammers, mills, and pulverizers, and the like.

Generally, a porous biocompatible material is manufactured and granules are obtained before the porogens are extracted. With porogens present, the material has increased physical integrity, allowing it to better withstand granulization. The porous biocompatible biomaterial can also be formed into granules after extraction of the porogens. An exemplary suitable method for polymers comprises freezing the material into rigid form before grinding. Detailed descriptions of preparing granules can also be found in co-pending International Patent Application No. PCT/US2010/26107 (in the name of Healionics Corporation, the assignee of the present disclosure), which is incorporated herein by reference in its entirety.

Granules obtained by any of the described methods may be subsequently sieved to obtain a preparation of granules that are substantially within a specific size range. There are both practical and biological considerations regarding size ranges of granules. Practically, manufacturing a porous granule of a size having a diameter that is only a few times the average diameter of the pores can be difficult. Further and in a biological context, following emplacement in vivo such granules may not present sufficient interstitial spaces to enable angiogenesis of larger blood vessels, and/or they may block continuity of a blood vessel channel between the granules. Accordingly to certain contemplated embodiments, granules that are too small, e.g., having less than about 0.1 mm diameter, should be discarded. Conversely, when granules are too large (e.g., more than 2 mm diameter), there may be insufficient tissue ingrowth through the porous biocompatible material and the granules may be difficult to apply or position.

In certain embodiments, the sizes of the granules are expressed in terms of dimensions (e.g., diameters) as determined by passing through a mesh or sieve having specifically sized mesh openings. In particular, granules may be sieved or otherwise sized to yield a size range from about 0.1 mm to about 2 mm, from about 0.1 mm to about 1 mm, from about 0.1 mm to about 0.8 mm, from about 0.1 mm to about 0.6 mm, from about 0.1 mm to about 0.4 mm, from about 0.1 mm to about 0.2 mm, from about 0.2 mm to about 2 mm, from about 0.2 mm to about 1 mm, from about 0.2 mm to about 0.8 mm, from about 0.2 mm to about 0.6 mm, from about 0.2 mm to about 0.4 mm, from about 0.2 mm to about 0.3 mm, from about 0.3 mm to about 2 mm, from about 0.3 mm to about 1 mm, from about 0.3 mm to about 0.8 mm, from about 0.3 mm to about 0.6 mm, from about 0.3 mm to about 0.5 mm, from about 0.4 mm to about 2 mm, from about 0.4 mm to about 1 mm, from about 0.4 mm to about 0.8 mm, from about 0.4 mm to about 0.6 mm, from about 0.5 mm to about 2 mm, from about 0.5 mm to about 1 mm, from about 0.5 mm to about 0.8 mm, from about 0.6 mm to about 2 mm, from about 0.6 mm to about 1 mm, from about 0.8 mm to about 2 mm, from about 0.8 mm to about 1 mm, from about 1 mm to about 2 mm. Granules larger than the desired range may be reground and sieved. For sieving, the dimensions above apply only to the least dimension of the granules.

In other embodiments, the size of a granule can be expressed as the diameter of a sphere that has substantially the same volume. Thus, when a granule is characterized by its "diameter equivalent" it should be understood that the term refers to the diameter of a sphere with substantially the same volume as a granule. "Substantially the same" refers to at least 70, 75, 80, 85, 90, 95, 96, 97, 98 or 99% and not more than 130, 125, 120, 110, 105, 104, 103, 102, 101 or 100% of the volume of the granule.

The granules prepared as described herein are, although generally irregularly-shaped, approximately spherical in shape or have an aspect ratio of no more than 5, or more preferably, no more than 4, or more preferably no more than 3 (see, e.g., FIG. 1). The term "aspect ratio" refers to the ratio of the largest dimension divided by the smallest dimension of a granule. In various embodiments, the aspect ratio may or may not be the same as the height to width ratio of a granule that forms a peak. As described herein, the heights of granules in a monolayer of the same correlate to the height of the peaks of the surface macrotopography, as defined herein.

Following preparation of granules and any size selection, the porogens may be extracted by chemical or physical method appropriate to the composition of the porogen and of the granules (i.e., the biocompatible material). Optionally, granules may then be coated or impregnated with a chemical or biological substance, such as a drug, growth factor, or sensor of body condition. Coating may be accomplished by dipping (or by suspending, bathing, rinsing, spraying, etc., or other method of contacting) granules in the chemical or biological substance, presented either in liquid or dry form. More uniform and quantitative coating can be obtained with the chemical or biological substance in liquid form. Higher amounts of loading can be obtained by first swelling the granules in a solvent. For example, soaking silicone granules in a protein-loaded suspension or solution comprising a solvent such as isopropanol causes the silicone to swell and take up the protein-loaded liquid. The solvent is then evaporated, resulting in granules that have incorporated the protein (or other chemical or biological substance) into the bulk. The choice of a solvent will depend in part on the composition of the biocompatible material and of the substance to be loaded. A solvent that swells the biomaterial substrate and dissolves the substance without deactivating the substance may be desirable in these and related embodiments. Any substance that dissolves in a solvent without deactivating the substance can be incorporated this way. Solvents for the substance that do not swell the biomaterial substrate may also be used to load the substance into the pore surfaces or open volumes without incorporating the substance into the bulk of the substrate. Some suitable solvents include xylene and other benzene derivatives, isopropanol, acetone and other ketones, and chlorohydrocarbons such as dichloromethane.

Chemical substances may, in certain contemplated embodiments, include chemicals that are sensitive to a stimulus, such as ultrasound, electrical impulse, electromagnetic radiation, light, or temperature. These may include chemicals that are sensitive to levels of oxygen or glucose in the body and that are capable, for instance, of displaying glucose-proportional fluorescence when activated by light. Molecules capable of exhibiting glucose-sensitive fluorescence include fluorescein isothiocyanate-labeled dextran, concanavalin A, rhodamine-concanavalin A, glucose oxidase, glucose dehydrogenase, hexokinase/glucokinase, bacterial glucose-binding protein, and boronic acid derivatives. Biological substances may, in certain contemplated embodiments, include growth factors (e.g., fibroblast growth factors, stem cell growth factors, platelet-derived growth factor, transforming growth factor beta, insulin-like growth factors, epidermal growth factor, vascular endothelial growth factor, angiopoietins, interleukins, granulocyte-colony stimulating factor, granulocyte macrophage colony stimulating factor, nerve growth factor, and keratinocyte growth factor), vitamins (e.g., vitamin A, vitamin C, vitamin E), fibrinogen, fibronectin, bone morphogenetic proteins, cytokines such as interleukins, lymphokines, chemokines, tumor necrosis factor-α, and interferons, leptins, cell adhesion molecules or portions thereof (e.g., RGD peptides, ICAM, NCAM, VCAM, integrins, CD44), antibacterial compounds or peptides, and enzymes (e.g., collagenase, plasminogen activator, proteases).

Granules may also be surface-modified with substances that are hydrophilic, such as polyethylene glycol or tetraglyme or alumina; and/or that are hydrophobic, such as polytetrafluoroethylene or silicone; and/or that increase lubricity, such as hyaluronic acid; and/or that improve cell adhesion, such as carbonyldiimidazole (with or without coupled proteins such as collagen); and/or that are radiopaque, such as noble metals; and/or or that are antimicrobial, such as silver ions or antimicrobial peptides, among others. For example, modifying the surfaces of granules with RGD (arginine-glycine-aspartic acid) peptides may increase cell adhesion to granules.

Granules may also be sterilized in a variety of ways. The granules may be sterilized with ethylene oxide gas, irradiated, autoclaved, or soaked in organic solvents, or sterilized by other ways known to those skilled in the art.

Typically, granules are attached to a device body by any known methods of effecting adherence. In certain embodiments, the granules are attached directly to a device body. In other embodiments, an intermediate layer (e.g., an adhesive or a conformal sheath) is interposed between the granules and the device body, wherein the intermediate layer covers a part of or an entire native surface of the device body.

Thus, a related embodiment provides a method for forming an implantable device having a device body and a microporous surface layer, comprising:

(a) forming a microporous biomaterial;
(b) grinding or dividing the microporous biomaterial into granules; and
(c) adhering the granules of the microporous biomaterial to a surface of a device body.

An exemplary method for attaching granules is to apply an adhesive material to one or more surfaces of the device and then contact the granules into the adhesive as diagrammatically shown in FIG. 4. Granules may, for example, be sprinkled on, or the device may be rolled in granules, or granules may be sprayed on the device, or applied with a tool or machine. The granules are contacted with the device, or with an adhesive, at least to the extent that surface portions of the granules are in contact with the adhesive. This will leave the interior of the granules and some surfaces of the granules substantially free of adhesive, to allow for tissue in-growth. The adhesive may then be cured, if necessary, before the device is put into use. Additionally or alternatively, granules may comprise or contain a substance that can act as a glue (as used herein, the terms "adhesive" and a "glue" are used interchangeably) under appropriate conditions. The glue in the granules may be appropriately activated (e.g., by heat, chemical, or light) and the granules may be contacted with the device.

For most purposes, the adhesive is biocompatible. Some biocompatible adhesives are silicone, fibrin, fibrinogen, chitosan, calcium phosphate cement, polyurethanes, gelatin, methacrylates, epoxyamine and hydrogels. Example materials appropriate for adhesion of the granules to a device surface include silicones such as Nusil MED 6400, Nusil MED-2214, or Nusil MED2 4213, Many biocompatible adhesives derive from nature. For example, natural glues may include those produced by a variety of marine animals (e.g., mollusks, sea stars), worms, bacteria, fungi, amphibians, spiders, insects, and algae (Graham, "Biological Adhesives from Nature" in *Encyclopedia of Biomaterials and Biomedical Engineering*, Eds. Bowlin and Wnek, Informa Healthcare, 2005; DOI 10.1080/E-EBBE-120041680; reference article incorporated in its entirety). Other biocompatible adhesives are well known in fields of wound dressings, dentistry, surgery, especially bone surgery and tissue repair and drug delivery via patches.

For some applications it may be advantageous to prepare an elastic conformal sheath or overcoat for the device body, and to first attach the granules to this sheath. Usually the sheath will be made from an elastic polymer and constructed over a mandrel reproducing the dimensions of the target device. Frequently the mandrel will be made in the same proportions as the target but undersized by about 5% to about 25% in dimensions, most often by about 10% to 20%. This allows the sheath to be elastically form fitted to the target device. It may be adhered to the device to retain location or prevent fluid ingress. Typically the sheath will have at least one opening to allow removal from the mandrel and placement on the target device.

Use of such a sheath covered with granules is of particular utility when the processes required to adhere granules directly to a device surface are incompatible with the device materials. For example the temperature required to cure granule attachment adhesive may be in excess of that tolerated by the target device. Other situations may include mechanical forces or chemical interactions.

Such a sheath may have substantially continuous walls other than at the opening or on other useful occasions be made of a mesh or other structure providing fluid communication through the thickness of the sheath after the granules are applied.

It will be understood that the necessary opening in the sheath may be filled by a variety of means after the granule coated sheath is applied to the device. Such means may include but are not limited to; solid elastomeric sheets, sheets of porous material, further sheets of granule covered material, active sensor or activator ports, electrical, pneumatic fluid or other connections.

Generally, granules will be applied to the surface of the device body (with or with the intermediate layer) in such a way that the granules form a monolayer with a desired surface coverage. In certain embodiments, all native surfaces of the device are covered in granules (i.e., surface coverage is or close to 100%). In other embodiments, however, it may be desirable to leave one or more areas of the device bare of granules. Other devices may, for instance, be attached directly to the device, or a sensor or biostimulating portion of the device may operate by direct tissue contact, or some other device portion may desirably remain uncovered. In such cases, granules may be attached to only a portion of the device. Masking means as commonly employed to control the deposition of materials on a surface may be used to create the desired pattern.

Textured Surface Layer With Continuously Porous/Open-Cell Construction

Figure 9:
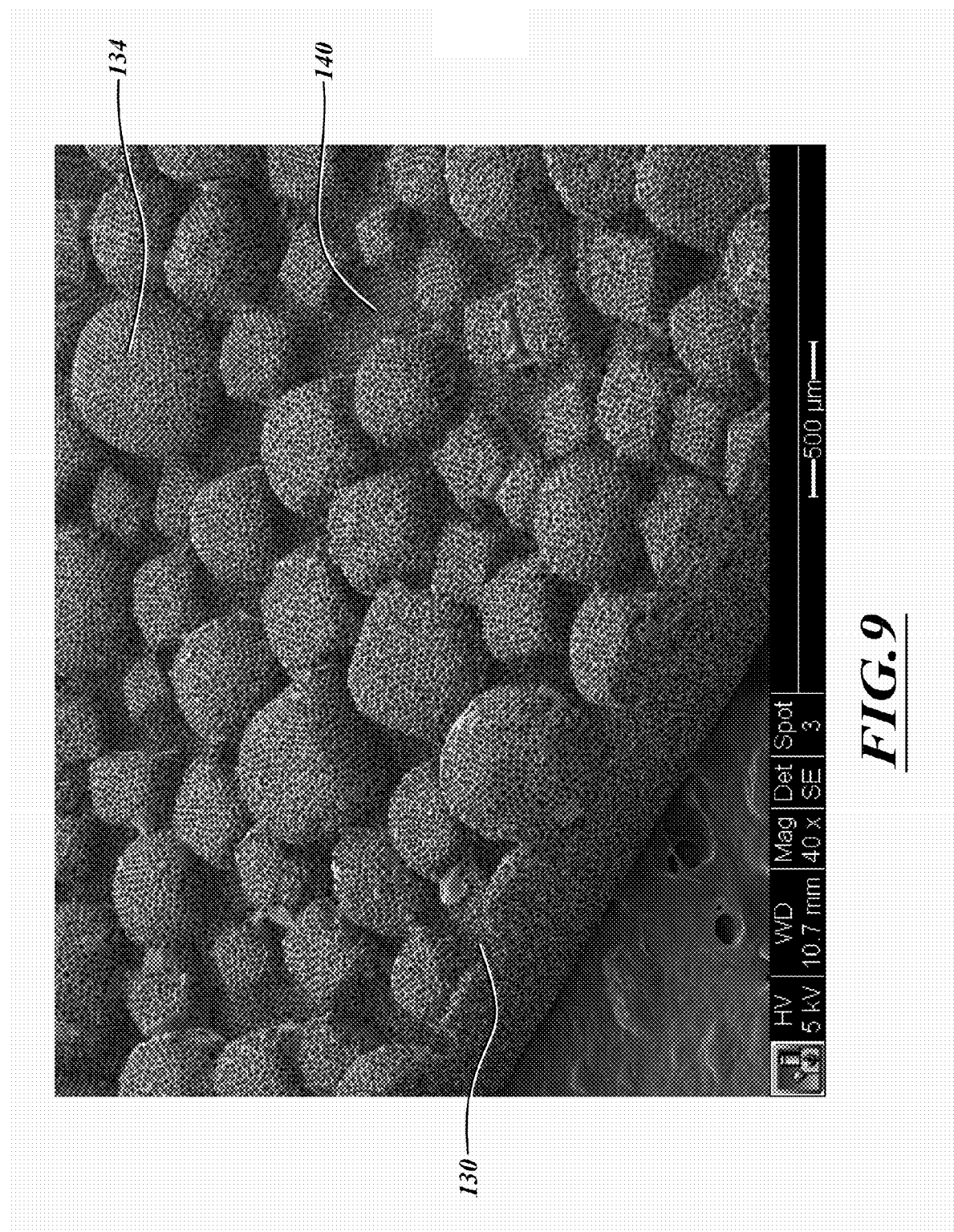
FIG. 9 is an SEM of a continuously microporous silicone scaffold with macrotopographic features.
Figure 10:
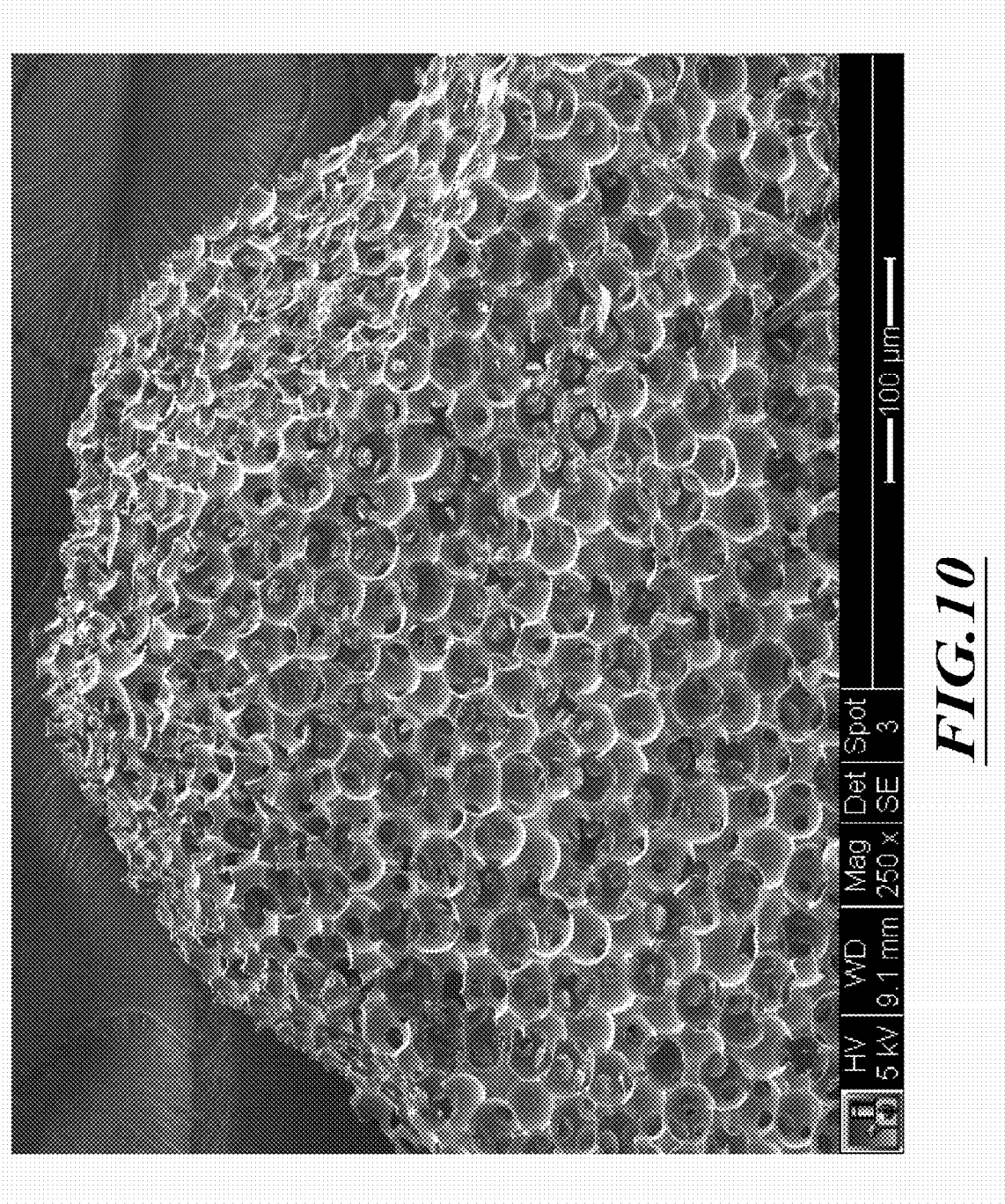
FIG. 10 is an SEM of a single peak of a continuously microporous silicone scaffold with macrotopographic features.

In other embodiments, as an alternative structure to a granular surface layer, the microporous surface layer has a continuous contour with surface macrotopographic features. The microporous surface layer may include interconnecting micropores throughout the entire layer in a continuous open-cell construction. FIG. 9 is an SEM of a continuous open-cell scaffold 130. As shown, substantially all of the tops and sides of the peaks 134, and bottoms of the depressions or valleys 140 between the peaks, contain continuously interconnecting pores, which enable cellular ingrowth into the open-cell structure. FIG. 10 shows the microporous structure of a single peak of a continuous open-cell scaffold.

Thus, one embodiment provides a microporous biomaterial with macrotopographic surface features, wherein the microporous biomaterial has a continuous contour and continuously interconnecting pores, wherein substantially all the pores are each interconnected to at least 2 other pores, a mean diameter of the pores is between about 5 and about 100 micrometers, and any two adjacent pores are connected by a throat, a mean throat diameter of the throats being between about 5 micrometers and about 50 micrometers, and wherein the macrotopography is defined by a plurality of peaks and valleys, wherein each peak comprises a plurality of pores and has a height of between about 100 micrometers and about 2000 micrometers.

A further embodiment provides an implantable device having a device body and a microporous biomaterial with macrotopographic surface features, wherein the microporous biomaterial has continuously interconnecting pores, wherein substantially all the pores are each interconnected to at least 2 other pores, a mean diameter of the pores is between about 5 and about 100 micrometers, and any two adjacent pores are connected by a throat, a mean throat diameter of the throats being between about 5 micrometers and about 50 micrometers, and wherein the macrotopography is defined by a plurality of peaks and valleys, wherein each peak comprises a plurality of pores and has a height of between about 100 micrometers and about 2000 micrometers.

In various embodiments, the height of the peaks that define the macrotopographic features can be between 100 and 2000 micrometers in heights, between about 200 micrometers and about 1000 micrometers, between about 500 micrometers and about 2000 micrometers, or between about 500 micrometers and about 1000 micrometers. More preferably, the height of the peaks will be between 300 and 500 micrometers.

In another embodiment, the microporous surface layer has a thickness of at least 40 micrometers while excluding the height of the peaks.

The continuously porous open-cell construction is suitable as a surface layer for implantable devices that measure or monitor certain analytes in the tissue. The open-cell structure allows analytes to pass through the pores of the microporous surface layer from the surrounding tissue to the device body, as in the case of a glucose monitor. In certain other embodiments, the implantable device delivers drugs, proteins, or biologic agents, which pass through the pores of the microporous surface layer to reach the surrounding tissue, as in the case of a pancreatic islet isolation capsule.

Macrotextured surface with continuously porous features (including the surfaces at the floors of the valleys between the peaks) is particularly advantageous for providing increased promotion of local angiogenesis in capsule tissue surrounding the biomaterial (see, FIG. 15). The increase in porous surface area due to the macrotopography allows more proangiogenic factors to be released into the adjacent tissue than can be delivered with a flat porous surface. Devices for which increased local angiogenesis is useful include biosensors (such as glucose sensors), immunoisolation devices (such as devices containing transplanted pancreatic islet cells), and tissue regeneration scaffolds.

The microporous scaffold in a continuously porous open-cell structure can be prepared by employing (1) micro-porogens as templates for forming the micropores throughout the scaffold (as discussed above) and (2) macro-porogens as templates for forming the surface macrotopographic features. As used herein, "macro-porogens" refers to a porogen sized so that a sphere of the same volume has a diameter ranging from about 100 micrometers to about 2000 micrometers. Suitable material for macro-porogens includes salt crystals and the like. The macrotopography can also be defined by known methods including rapid prototyping.

Thus, a further embodiment provides a method for forming a microporous biomaterial with macrotopographic features, the method comprising:

(a) arranging macro-porogens to form a template for a dissolvable mold surface with macrotopographic mold features, wherein the macro-porogens have a mean macro-porogen diameter that is between about 100 and about 2000 micrometers;

(b) removing the macro-porogens from the mold surface of (a) by chemical dissolution;

(c) filling the macrotopographic mold features with micro-porogens such that points of contact and interstitial spaces between adjacent micro-porogens are formed, wherein the micro-porogens have a mean micro-porogen diameter that is between about 5 micrometers and about 100 micrometers;

(d) fusing the micro-porogens together and to the mold surface at the points of contact;

(e) introducing a liquid biocompatible polymer precursor into the interstitial space between the micro-porogens;

(f) solidifying the biocompatible polymer precursor; and (g) removing the micro-porogens and the dissolvable mold surface.

In various embodiments, the macro-porogens can be removed by, for example, solvent dissolution or chemical dissolution. For instances, macro-porogens formed of salt crystals can be dissolved by water. Macro-porogens formed of polymer beads can be dissolved by an organic solvent.

In other embodiments, solidifying the biocompatible polymer precursor can be accomplished thermally (e.g., curing) or chemically (e.g., polymerization).

In certain embodiments, the dissolvable mold surface is poly(methyl methacrylate) or polystyrene.

The micropores can also be formed by a number of known methods for forming open-cell porous materials, including, but not limited to, gas foaming, particle sintering, salt-leaching, polymer bead leaching, phase separation, and rapid prototyping.

It should also be understood that while FIG. 9 shows the macrotopography as hills and valleys on one side of the substantially flat porous base portion, that the macrotopography may be formed from both surfaces of such a base, or in general to any shape of a substantially continuous base.

Reducing Foreign Body Responses

As Example 4 demonstrates, implanted devices that have a textured, microporous surface layer integrate better with the surrounding tissue, thus avoiding buildup of dense avascular scar and other undesirable effects caused by foreign body responses. In particular, the surface texture or macrotopographic features, such as peaks and valleys formed by porous granules attached to the device as described herein, wherein portions of the nonporous device surface or other intermediate layer are exposed in the valley floor, allowing tissue penetration into the micropores and between the peaks of the surface macrotopographic features while managing the degree of vascularization within the valleys. With improved integration of the device body with the surrounding tissue, the potential formation of a fibrotic capsule around the implanted device can be minimized or eliminated. The peaks and valleys that define the macrotopography of the microporous biomaterial surface layer interfere with lattice contraction, complementing the vascularized interface by relieving stresses from collagen lattice contraction that normally exacerbate fibrotic buildup. FIG. 13 shows that alpha smooth muscle actin ($\alpha$-SMA)-positive myofibroblasts—the stress elements that are a hallmark of capsule scar tissue—are absent in the foreign body response to the microporous macrotextured biomaterial (E), suggesting a stress-relaxed condition.

Thus, one embodiment provides a method of implanting a microporous biomaterial with macrotopographic surface features, wherein the microporous biomaterial has continuously interconnecting pores, wherein substantially all the pores are each interconnected to at least 2 other pores, a mean diameter of the pores is between about 5 and about 100 micrometers, and any two adjacent pores are connected by a throat, a mean throat diameter of the throats being between about 5 micrometers and about 50 micrometers, and wherein the macrotopography is defined by a plurality of peaks and valleys, wherein each peak comprises a plurality of pores and has a height of between about 100 micrometers and about 2000 micrometers, and at least two adjacent peaks define a valley, the valley having a floor from which the heights of the adjacent peaks are measured.

A further embodiment contemplated herein provides a method comprising implanting an implantable device having a device body; and a microporous surface layer with macrotopographic features, wherein the microporous surface layer has continuously interconnecting pores, wherein substantially all the pores are each interconnected to at least 2 other pores, a mean diameter of the pores is between about 5 and about 100 micrometers, and any two adjacent pores are connected by a throat, a mean throat diameter of the throats being between about 5 micrometers and about 50 micrometers, and wherein the macrotopography is defined by a plurality of peaks and valleys, wherein each peak comprises a plurality of pores and has a height of between about 100 micrometers and about 2000 micrometers.

Another embodiment provides a method comprising implanting an implantable device comprising a device body; and a textured surface layer overlying the device body, wherein the textured surface layer comprises one or more granules of a microporous biomaterial, the granules forming a surface macrotopography that includes a plurality of peaks and valleys, each peak having a height of between about 100 micrometers and about 2000 micrometers, and wherein each granule comprises a plurality of interconnecting pores having a mean pore diameter of between about 5 and 100 micrometers, and any two adjacent pores are connected by a throat, a mean throat diameter of the throats being between 5 and 50 micrometers.

In further embodiments, the microporous biomaterial may comprise an open-cell structure throughout the entire microporous biomaterial.

In yet further embodiments, the surface of the floor of the valleys between the peaks is impermeable to fluids, In other embodiments, the surface of the floor of the valleys between the peaks is microporous.

In yet further embodiments, the microporous biomaterial is permeable to fluids or electrolytes.

A further embodiment provides a method for avoiding the thickening of a foreign body capsule that forms in a tissue around an implanted device as a result of foreign body response by implanting the implantable device with the surface features as described herein.

A further embodiment provides a method for promoting angiogenesis in and around an implanted device by implanting the implantable device with the surface features as described herein.

A further embodiment provides a method for reducing the risk of device-related infection by implanting the implantable device with the surface features as described herein.

Improving Resistance to Exit Site Infection

As Example 5 demonstrates, resistance to exit site infection for catheters and other percutaneous devices that breach the skin barrier can be improved by using a macrotextured microporous silicone cuff at the skin line. In contrast to Dacron felt cuffs that are typically placed subcutaneously 1-2 cm away from the exit site, the macrotextured microporous silicone cuff is effective when it is used at the skinline to span the exit site. The special combination of macrotexturing and microporosity prevents the leading edge of the epidermis from migrating inward along the surface, thereby preventing sinus tract formation.

The pore structure promotes stable ingrowth of the epidermis and dermis. Also, the size of the pore throats can be optimized to ensure that macrophages and other host antimicrobial defense cells can gain access to every pore. This avoids the infection risk problem of polydisperse pore size biomaterials that have pores too small for host cell access but still large enough for bacteria to enter and fester. The optimized pore size maximizes the concentration of antimicrobial host cells and may promote release of antimicrobial factors. The macrotexturing increases the surface area of biomaterial in contact with the surrounding tissue, potentially amplifying antimicrobial effects.

The following examples are offered by way of illustration, and not by way of limitation.

EXAMPLES

Example 1

Manufacture of Granules Formed of Poly(2-hydroxy-ethyl methacrylate)

This example describes production of granules made of a porous biocompatible material.

Poly(methyl methacrylate) (PMMA) beads with diameter 36 micrometers +/−2 micrometers were added to polyether ether ketone (PEEK) molds consisting of a cavity about 3 cm long×2 cm wide×0.5 cm deep, and sintered for 19 hours at 190° C. to give neck sizes of about 40% of the bead diameter. These fused-bead pore templates were infiltrated with a polymer precursor comprising the components in Table 1.

TABLE 1

| Polymer Precursor Mixture | |
| --- | --- |
| COMPONENT | VOLUME (ML) |
| 2-hydroxyethyl methacrylate (HEMA) | 7.0 |
| Ethylene glycol | 2.1 |
| Tetraethylene glycol dimethacrylate | 0.31 |
| Ammonium persulfate (0.4 g/mL) | 0.7 |
| Sodium metabisulfite (0.15 g/mL) | 0.7 |
| Endotoxin-free water | 1.4 |

The mixture was allowed to polymerize for 24 hours to provide polyHEMA impregnated with PMMA beads. The polymer was ground with a rotary blade coffee grinder. Granules were sieved, and the size fraction passing through 0.7 mm openings, but retained by 0.3 mm openings, was collected for use.

The PMMA pore templates were removed from the granules by Soxhlet extraction in dichloromethane.

The granules were transferred to acetone to swell the polyHEMA, then rinsed by Soxhlet extraction in endotoxin-free water for 2 hours with the condenser turned off (to boil off the acetone and dichloromethane) followed by 4 hours of Soxhlet rinsing with the condenser running.

Example 2

Manufacture of Granules Formed of Silicone

Monodisperse 27 μm thermoplastic acrylic beads were thoroughly sieved between meshes of 25 μm and 35 μm opening sizes using a RX-29 RoTap automatic sieve shaker (WS Tyler, Mento, Ohio) to remove undersized beads as well as any macro size particulate contaminants larger than the beads.

The beads were transferred to a rectangular mold (3 cm×2 cm×1 cm) and placed in a convection oven for 20 h at 180° C. to sinter the beads to approximately 11 μm interbead neck diameter.

The sintered bead "brick" was removed from the mold and impregnated with catalyzed NuSil MED-4211 silicone by centrifugation for 1 h at 30,000-g. After impregnation with silicone, the brick was placed in an oven at 80° C. for 16 h to cure the silicone.

Excess silicone was peeled from the outer surfaces of the brick to ensure that no granules would have surfaces skinned over with silicone.

A rotary blade coffee grinder was used to grind the brick into granules approximately 400 µm in diameter. The granules were then thoroughly sieved with a RoTap automatic sieve shaker to remove particles smaller than 300 µm or larger than 500 µm. Light microscopy was used to verify that >90% of granules of were within the target range.

Following sizing, the granules were stirred in dichloromethane for an initial extraction of the acrylic beads. Soxhlet extraction in dichloromethane was used to remove residual acrylic. Subsequent Soxhlet rinses in acetone followed by endotoxin-free water were used to boil off residual solvents. Scanning Electron Microscopy (SEM) was used to verify that mean throat size of the granules was between 10 and 12 µm.

Example 3

Application of Granules to Surface of Device

To form a substrate onto which the granules are applied, a 0.6 mm layer of Dow Corning MDX4-4210 silicone was cast in a mold and cured per manufacturer's guidelines. NuSil MED-6400 silicone was mixed and degassed by centrifugation, then poured over the MDX4-4210 sheet. The substrate was oriented vertically to allow the excess MED-6400 allowed to flow off. The xylene solvent (a component of the MED-6400) was allowed to evaporate to leave a high-viscosity adhesive surface.

The dry granules prepared according Example 2 were spread over the adhesive-coated surface, and the adhesive was allowed to wick approximately 100 µm into the pore structure of the granules. The adhesion layer was then cured with a ramped curing cycle per the manufacturer's guidelines. A typical granule-coated surface is pictured in the SEM image in FIG. 5.

Example 4

Macrotextured Microporous Surface Structure Reduces Fibrotic Encapsulation of Subcutaneous Silicone Implants Materials and Methods Silicone disks (10-mm diam., ~1-mm thickness) with various surface geometries were subcutaneously implanted into the dorsum of domestic swine for 6 weeks. All disks comprised a nonporous central core plus the test surface on both sides, and all test implants were formed from unrestricted long-term implant-grade NuSil silicones with ~30 Shore A durometer. All disks were Soxhlet-extracted in endotoxin-free water at 100° C. for 6 hours and autoclave-sterilized prior to implantation.

Test surface configurations included (A) smooth (nonporous and without surface texture) controls (n=8); (B) nonporous macrotextured surfaces (n=24) with features in the 300-500 µm size range (Allergan Biocell®, Mentor Siltex®, and a surface with salt crystal-shaped projections); (C) a non-textured, sphere-templated microporous structure (n=8) with interconnected ~27-30-µm pores (Healionics STAR® biomaterial); (D) a continuously porous macrotextured version of STAR; and (E) a macrotextured microporous structure (Healionics STARsprinkles™) with intermittent nonporous surface at the valley floors. The macrotextured microporous structure was fabricated by fragmenting STAR biomaterial into (300-500 µm) porous granules and applying a monolayer of granules to a silicone surface with a dip-coated silicone adhesion layer (n=24). The non-porous surface comprised exposed portions of the silicone adhesion layer and/or the native surface of the disk.

After sacrifice, the disks and surrounding tissue were excised. Using ethanol-based xylene-free processing techniques, the samples were paraffin embedded, cross-sectioned, and H&E stained or immunostained for alpha smooth muscle actin (α-SMA). For each sample, a stitched montage of the entire 10 mm disk cross section (H&E images) was used to measure foreign body capsule thickness every 300 µm along both the skin- and muscle-facing sides of the implant (excluding the regions within 500 µm from each edge). Student's unpaired t test was used to determine statistical significance between groups.

Results

Figure 11:
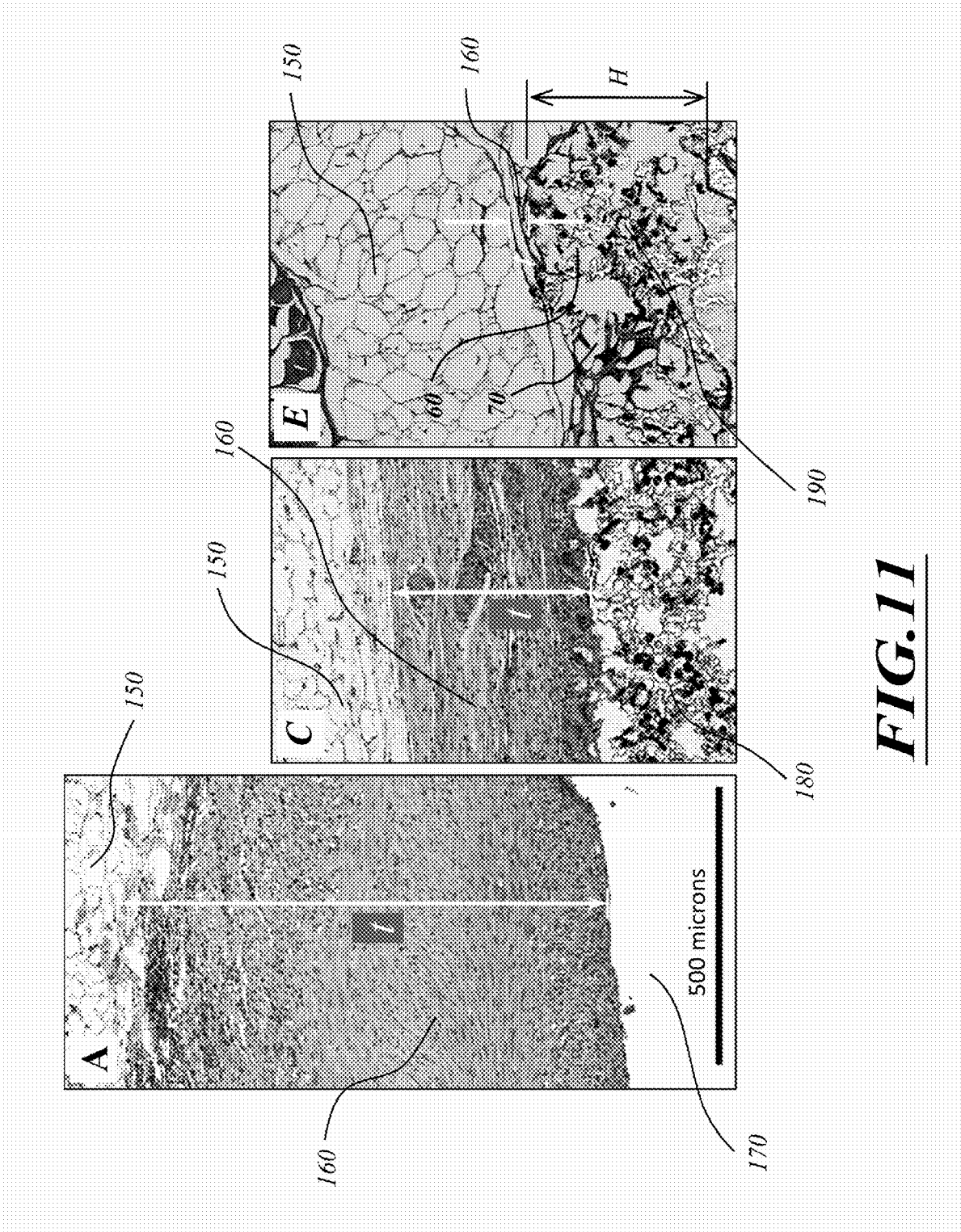
FIG. 11 shows Hematoxylin and Eosin stained histological sections of the tissue-implant interfaces for three biomaterial surface geometry configurations. The foreign body response and capsule thickness after subcutaneous implantation for 8 weeks in a pig model is compared. Panel A: Smooth nonporous silicone; Panel C: Flat microporous Silicone with 27-micron pore size; and Panel E: Macrotextured microporous silicone in accordance with an embodiment of the present disclosure.

FIG. 11 shows H&E-stained histological sections of the foreign body response to (A) smooth nonporous control, (C) flat microporous, and (E) macrotextured microporous biomaterial with intermittent nonporous surfaces at the valley floors between the peaks. The thickness t of the capsule tissue 160 that separates the tissue-biomaterial interface from the surrounding adipose tissue 150 is thickest in Panel A for the smooth nonporous control biomaterial 170, where capsule tissue 160 is dense and avascular. Panel B shows an intermediate capsule response next to the vascularized porous silicone biomaterial 180. Panel C shows that the capsule tissue 160 is very thin (almost absent) and vascularized in the interface region across the top of the peak 60 of the vascularized macrotextured microporous silicone biomaterial 190. The valley 70 contains vessel-rich tissue rather than dense fibrous capsule tissue. The height H of the macrotopographic microporous surface layer is indicated.

Figure 12:
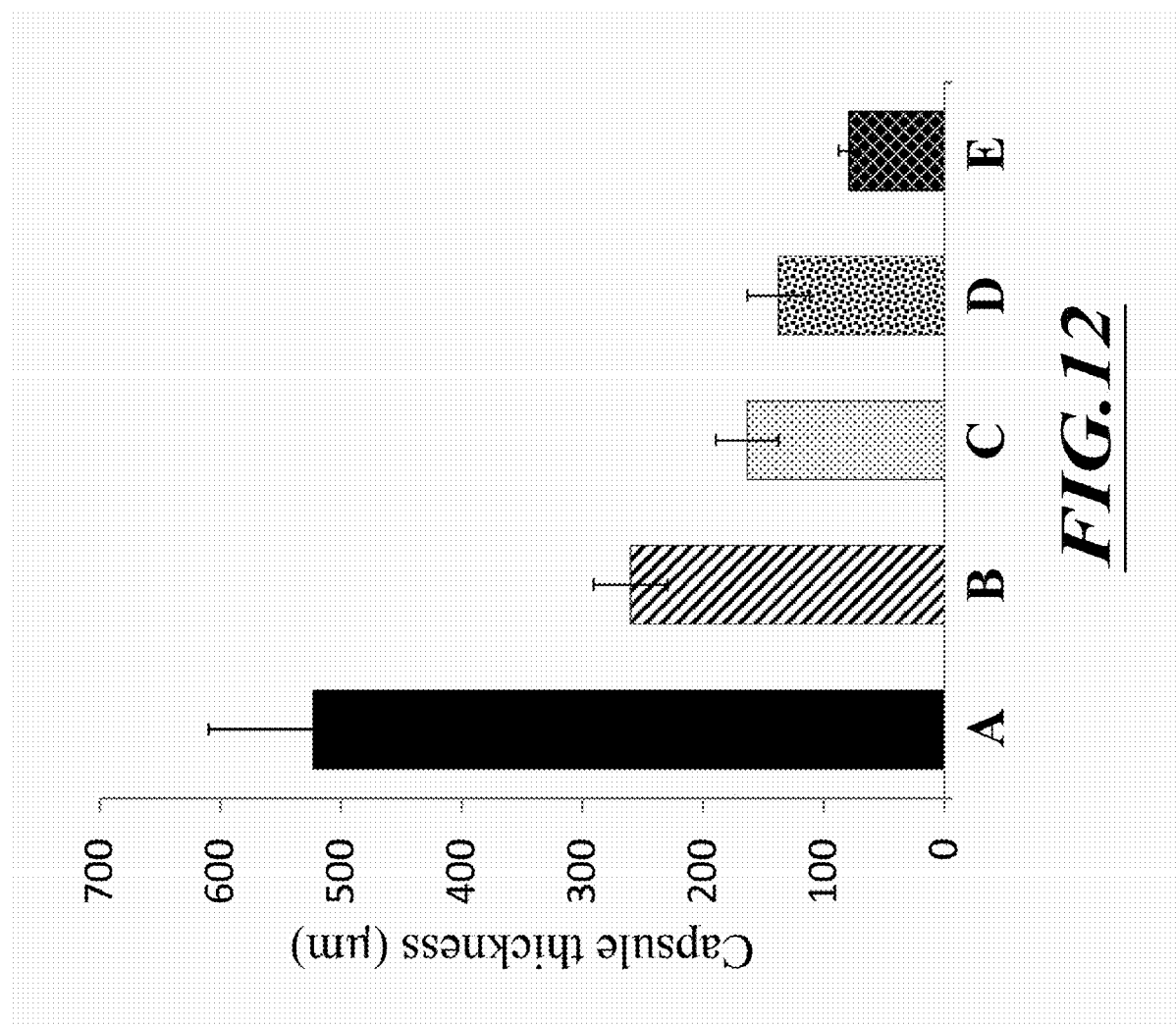
FIG. 12 is a column chart comparing the measured mean foreign body capsule thickness after implanting silicone biomaterials with four different surface geometry configurations. Column A: smooth nonporous surface; Column B: textured nonporous surface; Column C: 27-micron porous surface; Column D: macrotextured and continuously microporous surface; and Column E: macrotextured and intermittently microporous surface.

FIG. 12 shows that the average capsule thickness depends strongly on the implant surface geometry. The macrotextured microporous STARsprinkles surface with intermittent nonporous surface (E) was significantly more effective at reducing foreign body encapsulation than either texture (B) ($p<0.0001$) or microporosity (C) ($p<0.005$) used alone. The capsule tissue surrounding the microporous surfaces (flat sheet STAR, macrotextured continuously porous STAR, or STARsprinkles) was less dense, less granulomatous, and more vascularized than the capsule surrounding nonporous surfaces. In addition and unexpectedly, the macrotextured microporous STARsprinkles surface with intermittent nonporous surface (E) was substantially more effective at reducing foreign body encapsulation than the macrotextured continuously porous surface (D).

Without wishing to be bound by any theory, it is hypothesized that the macrotopography from the granular STARsprinkles surface complements the microporosity-induced vascularized interface by relieving stresses from collagen lattice contraction that normally exacerbate fibrotic buildup. The usual layer of alpha smooth muscle actin positive myofibroblasts—the stress elements of the capsule and the hallmarks of capsule scar tissue—is absent, suggesting a stress-relaxed condition.

FIG. 13 shows alpha smooth muscle actin stained histological sections of the foreign body response to (A) Smooth nonporous control, (B) Textured nonporous surface (Prior Art), (C) flat microporous biomaterial (Prior Art), and (E) macrotextured microporous biomaterial. In Panel A, the thickness M of the myofibroblast layer 210 is very thick, with only the outer 10% of the capsule occupied by myofibroblast-free capsule tissue 220. In Panel B, the thickness M of the myofibroblast layer 210 is thinner than for A, occupying about half of the total capsule thickness. In Panel C, the myofibroblast layer 210 is thinner and less aligned than for A or B. In Panel E, the myofibroblast layer is absent (the only stained features are blood vessels).

Example 5

Skin Integration Cuff Improves Resistance to Exit Site Infections in Porcine Bacterial Challenge Patients who require percutaneous devices such as catheters are at high risk to acquire life-threatening infections. Despite surgical advances and improvements in device design and materials, a patient catheterized for four months has >50% probability of infection. One third to one half of these infections occur via the breach of the skin barrier due to inadequate sealing of the exit site between the device and the surrounding skin, especially with longer term uses. The ability of a new exit site cuff to protect against exit site infection was investigated. STARcuff™ (Healionics, Seattle, Wash.) combines precisely selected pore geometry with a textured macrotopography to form an integrated skin seal.

Methods

STARcuff test articles were given a macrotextured microporous biointerface layer by fragmenting sphere-templated silicone with 35-µm pores (as described in US Pat. App. 2008/0075752) into porous granules (300-500 µm) and applying a monolayer of granules to silicone tubing with a dip-coated silicone adhesion layer. In each of three 35-kg domestic pigs, 8-cm segments of 3-mm diameter silicone tubing were implanted percutaneously in the dorsum, with the exterior end sealed to prevent bacterial entry through the lumen. Six implants per pig contained a STARcuff biointerface layer positioned at the skinline, six were 'Dacron felt cuff only' controls with no STARcuff or antimicrobial cuff at or near the skinline, and another six (in 2 of 3 pigs) included a VitaCuff™ silver ion loaded antimicrobial cuff (Bard Access Systems, Salt Lake City, Utah). All three types of test articles included a subcutaneously positioned Dacron felt cuff (Bard's SureCuff™ or equivalent) to restrict motion by encouraging ingrowth of fibrous scar tissue. The test sites on both animals were sprayed with chlorhexidine antiseptic on days 0, 3, 7, and 14 and protected by gauze bandages. On day 27, the wound sites on 2 of the 3 pigs were inoculated by placing a porous polycarbonate ring loaded with S. aureus ($10^6$ to $10^8$ CFU) onto the skin around the implant. The rings were removed on Day 28. Digital photos and infrared thermography images were taken at days 0, 3, 7, 14, 21, 27, 28, 29, 30, and 31. The animals were euthanized on Day 31. All samples were harvested and submitted for histological analysis, with a 5-mm subcutaneous segment of tubing between 1 and 1.5 cm from the exit site and surrounding tissue excised from each sample for quantitative bacterial culture.

Results

Figure 16:
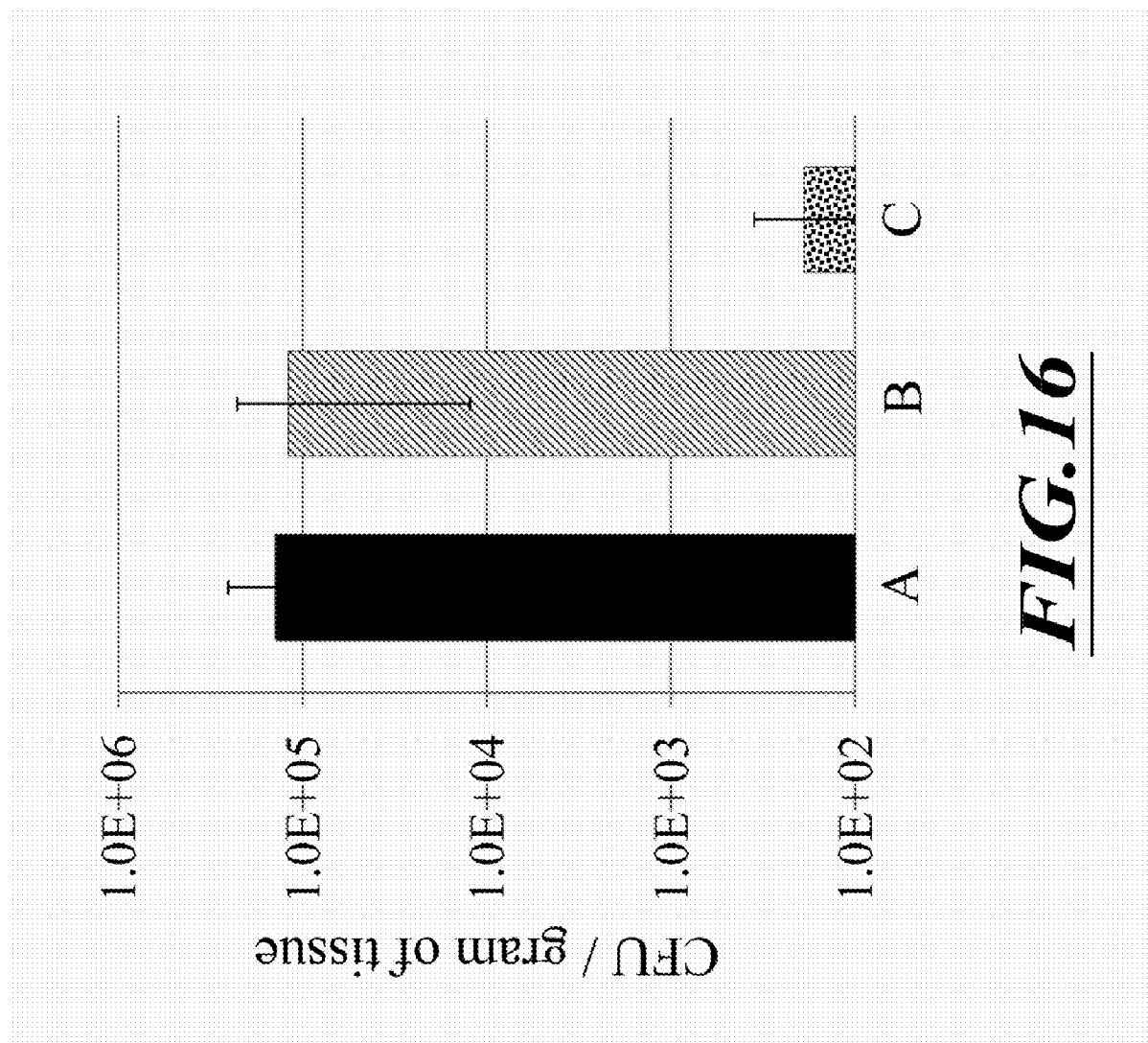
FIG. 16 is a column chart comparing the bacterial loads measured in the tissue for three different types of percutaneous catheter test implants following bacterial challenge. Column A: Felt Cuff Only control; Column B: Silver Eluting Cuff control; Column C: Macrotextured microporous exit site sealing cuff in accordance with an embodiment of the present disclosure.

From gross observations, 58% (7 of 12) of challenged Felt Cuff Only control exit site wounds showed mild signs of infection (purulent discharge and/or thicker pericatheter crust), compared to 33% (4 of 12) of VitaCuff controls and %0 of STARcuff exit sites. All Felt Cuff Only controls and 92% of VitaCuff controls showed signs of a sliding interface with increased inflammatory response, while all STARcuff exit sites appeared relatively healthy and tightly integrated with surrounding tissue. Quantitative culture results revealed viable CFUs in 58% of Felt Cuff Only controls, 42% of VitaCuff controls, and 17% of STARcuff exit sites, with arithmetic mean S. aureus log CFU counts of 5.1, 5.1, and 2.3 respectively as shown graphically FIG. 16.

IR thermography results showed that increased susceptibility to infection (defined as positive S. aureus culture at Day 31) correlated with elevated exit site skin temperature at Day 14 ($p=0.0003$) and Day 21 ($p=0.0002$).

Histology of Felt Cuff Only and VitaCuff exit sites showed epidermal downgrowth several mm along the wall of the tubing; beyond the edge of the epidermis, the implant-tissue interface contained dense granuloma, with a robust biofilm populated by gram-positive cocci evident in some cases. In contrast, STARcuff exit sites were characterized by vascularized dermal ingrowth into the pore structure, minimal epidermal downgrowth, reduced inflammatory response, and no biofilm.

CONCLUSIONS

STARcuff implants resulted in better-sealed, healthier exit sites than controls. Evidence from gross observations, quantitative culture, IR thermography, and histological analysis indicate that STARcuff improves resistance to exit site infection. VitaCuff did not show a significant effect on infection resistance when challenged 27 days post-implant, suggesting that its antimicrobial activity was depleted by the time of the challenge. Since STARcuff's effectiveness does not depend on release of an antimicrobial agent, it is hypothesized that it provides protection indefinitely. This approach can potentially pave the way for an improved standard of care for any percutaneous devices used for an extended duration, including dialysis catheters, abutments for prosthetics, ventricular assist devices, and others.

From the foregoing it will be appreciated that, although specific embodiments of the invention have been described herein for purposes of illustration, various modifications may be made without deviating from the spirit and scope of the invention. Accordingly, the invention is not limited except as by the appended claims.

The various embodiments described above can be combined to provide further embodiments. All of the U.S. patents, U.S. patent application publications, U.S. patent application, foreign patents, foreign patent application and non-patent publications referred to in this specification and/or listed in the Application Data Sheet are incorporated herein by reference, in their entirety. Aspects of the embodiments can be modified, if necessary to employ concepts of the various patents, application and publications to provide yet further embodiments.

The invention claimed is:

1. A microporous biomaterial with macrotopographic surface features and a plurality of pores, wherein substantially all the pores are each interconnected to at least 2 other pores, a mean diameter of the pores is between about 5 and about 100 micrometers, and any two adjacent pores are connected by a throat, a mean throat diameter of the throats being between about 5 micrometers and about 50 micrometers, and wherein the macrotopography is defined by a plurality of peaks and valleys, wherein each peak is porous and has a height of between about 100 micrometers and about 2000 micrometers, and at least two adjacent peaks define a valley, the valley having a floor from which the heights of the adjacent peaks are measured, wherein the surface of the floor of the valleys between the peaks is impermeable to fluids.

2. The microporous biomaterial of claim 1, wherein the biomaterial is permeable to fluids or electrolytes.

3. The microporous biomaterial of claim 1, wherein the mean pore diameter is between about 20 and about 40 micrometers.

4. The microporous biomaterial of claim 1, wherein the height of each peak is between about 100 micrometers and about 500 micrometers.

5. The microporous biomaterial of claim 1, wherein the height of each peak is between about 200 micrometers and about 1000 micrometers.

6. The microporous biomaterial of claim 1, wherein the height of each peak is between about 500 micrometers and about 2000 micrometers.

7. The microporous biomaterial of claim 1, wherein the height of each peak is between about 500 micrometers and about 1000 micrometers.

8. The microporous biomaterial of claim 1, wherein the biomaterial is biodegradable.

9. The microporous biomaterial of claim 1, wherein the biomaterial is a hydrogel, silicone rubber, expanded fluoropolymer, a polymer or a metal.

10. The microporous biomaterial of claim 1, wherein the biomaterial comprises a conductive polymer or metalized polymer.

11. The biomaterial of claim 1, wherein the biomaterial underlying the macrotopographic surface features has a thickness of at least 40 micrometers.

12. An implantable device comprising:
a device body; and
a microporous biomaterial overlying the device body wherein the microporous biomaterial has macrotopographic surface features and a plurality of pores, and wherein substantially all the pores are each interconnected to at least 2 other pores, a mean diameter of the pores is between about 5 and about 100 micrometers, and any two adjacent pores are connected by a throat, a mean throat diameter of the throats being between about 5 micrometers and about 50 micrometers, and wherein the macrotopography is defined by a plurality of peaks and valleys, wherein each peak is porous and has a height of between about 100 micrometers and about 2000 micrometers, and at least two adjacent peaks define a valley, the valley having a floor from which the heights of the adjacent peaks are measured, wherein the surface of the floor of the valleys between the peaks is impermeable to fluids.

13. The implantable device of claim 12, further comprising an intermediate layer interposed between the device body and the microporous surface layer.

14. The implantable device of claim 13, wherein the intermediate layer is an adhesive layer.

15. A method for promoting angiogenesis comprising: implanting the implantable device of claim 13.

16. An implantable device comprising:
a device body; and
a textured surface layer overlying the device body, wherein the textured surface layer comprises one or more granules of a microporous biomaterial, the granules forming a surface macrotopography that includes a plurality of peaks and valleys, each peak having a height of between about 100 micrometers and about 2000 micrometers, and wherein each granule comprises a plurality of interconnecting pores having a mean pore diameter of between about 5 and 100 micrometers, and any two adjacent pores are connected by a throat, a mean throat diameter of the throats being between 5 and 50 micrometers, and at least two adjacent peaks define a valley, the valley having a floor from which the heights of the adjacent peaks are measured, wherein the surface of the floor of the valleys between the peaks is impermeable to fluids.

17. The implantable device of claim 16 wherein the mean pore diameter is between about 20 and about 40 micrometers.

18. The implantable device of claim 16, wherein the height of each peak is between about 200 micrometers and about 1000 micrometers.

19. The implantable device of claim 16, wherein the height of each peak is between about 500 micrometers and about 2000 micrometers.

20. The implantable device of claim 16, wherein the height of each peak is between about 500 micrometers and about 1000 micrometers.

21. The implantable device of claim 16, further comprising an intermediate layer interposed between the device body and the textured surface layer.

22. The implantable device of claim 21, wherein the intermediate layer is an adhesive layer.

23. The implantable device of claim 21, wherein the intermediate layer is a conformal sheath that covers a part of or an entire native surface of the device body.

24. The implantable device of claim 20, wherein the textured surface layer covers more than 80%, or more than 90% of a total area of a native surface of the device body.

25. A method comprising: implanting the microporous biomaterial of claim 1.

26. The method of claim 25, wherein the microporous biomaterial is a surface layer overlying an implantable device.

27. A method for promoting angiogenesis comprising: implanting an implantable device comprising: a device body; and the microporous biomaterial of claim 1.

28. A method for promoting angiogenesis comprising: implanting the implantable device of claim 16.

* * * * *